United States Patent [19]
Cohen

[11] Patent Number: 4,899,752
[45] Date of Patent: Feb. 13, 1990

[54] SYSTEM FOR AND METHOD OF THERAPEUTIC STIMULATION OF A PATIENT'S HEART

[75] Inventor: Todd J. Cohen, Baltimore, Md.

[73] Assignee: Leonard Bloom, Towson, Md.

[21] Appl. No.: 201,935

[22] Filed: Jun. 3, 1988

Related U.S. Application Data

[63] Continuation-in-part of Ser. No. 105,030, Oct. 6, 1987.

[51] Int. Cl.⁴ .............................................. A61N 1/00
[52] U.S. Cl. .............................. 128/419 PG; 128/672; 128/673
[58] Field of Search ............. 128/419 PG, 672, 419 P, 128/673

[56] References Cited

U.S. PATENT DOCUMENTS 4,770,177  9/1988  Schroeppel .................. 128/419 PG
4,802,481  2/1989  Schroeppel .................. 128/419 PG Primary Examiner—Francis Jaworski
Assistant Examiner—George Manuel
Attorney, Agent, or Firm—Leonard Bloom

[57] ABSTRACT

A system for therapeutic stimulation of a patient's heart includes means for varying the escape interval or rate of a means for producing pacing pulses. Pressure sensing means sense pressure at a site in the circulatory system of a patient. Signal producing means respond to output from the sensing means to develop a variable first signal representative of mean pressure at the site over a period of predetermined duration. Signal producing means respond to output from the sensing means for developing a second signal representing mean pressure at the site over a period of given duration less than the period of predetermined duration. Control signal producing means responsive to the first signal and to the second signal develop a control signal upon the first signal and the second signal differing by at least a predetermined amount. Control means, responsive to the control signal, control the means for varying the escape interval or rate of the means for producing pacing pulses. The escape interval or rate may be additionally controlled by a second control signal related to the activity level of the patient either conjointly or contemporaneously. A method of therapeutic stimulation of a patient's heart is also disclosed. The method can be viewed as an analogue of the system.

40 Claims, 11 Drawing Sheets

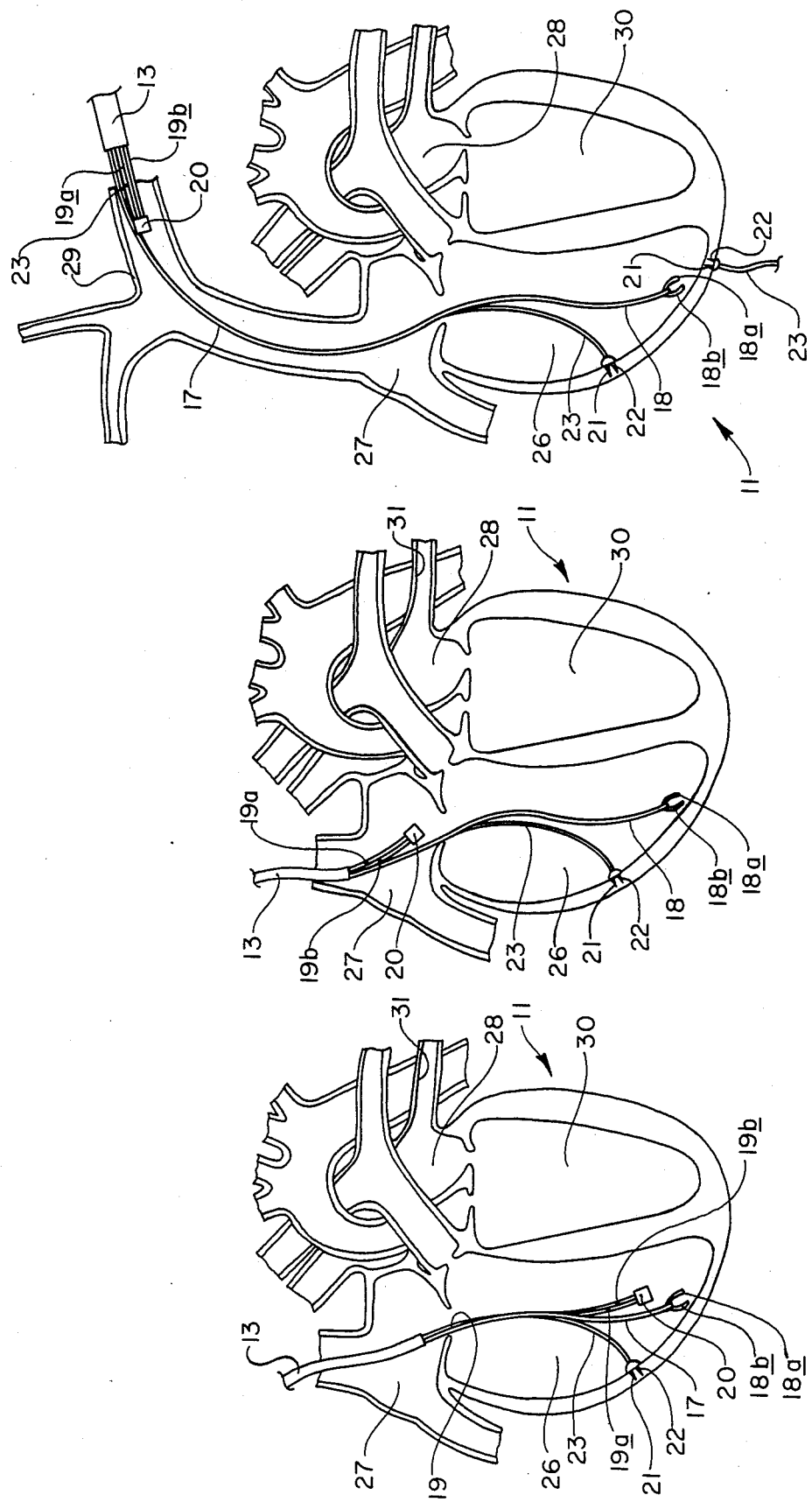

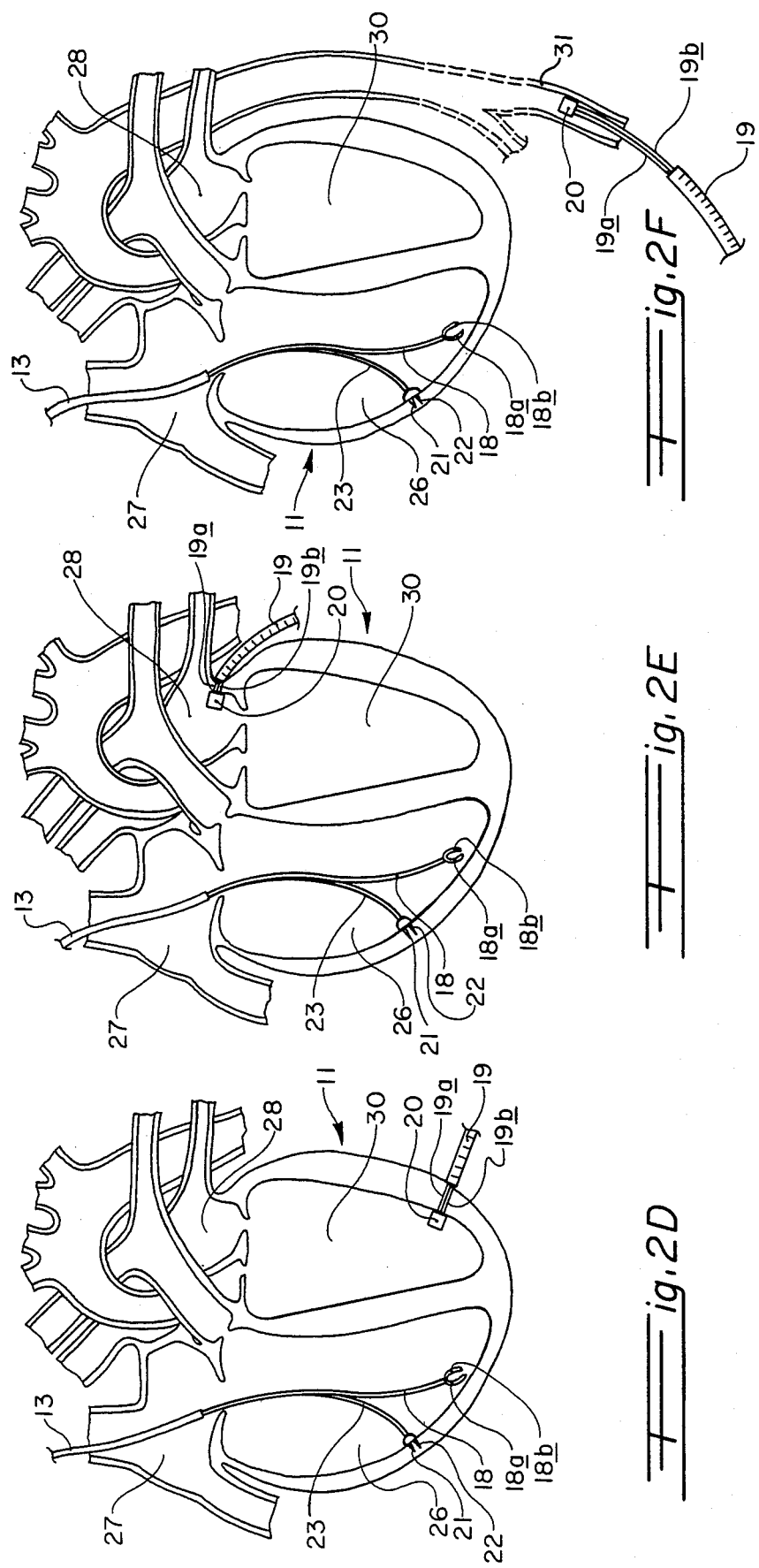

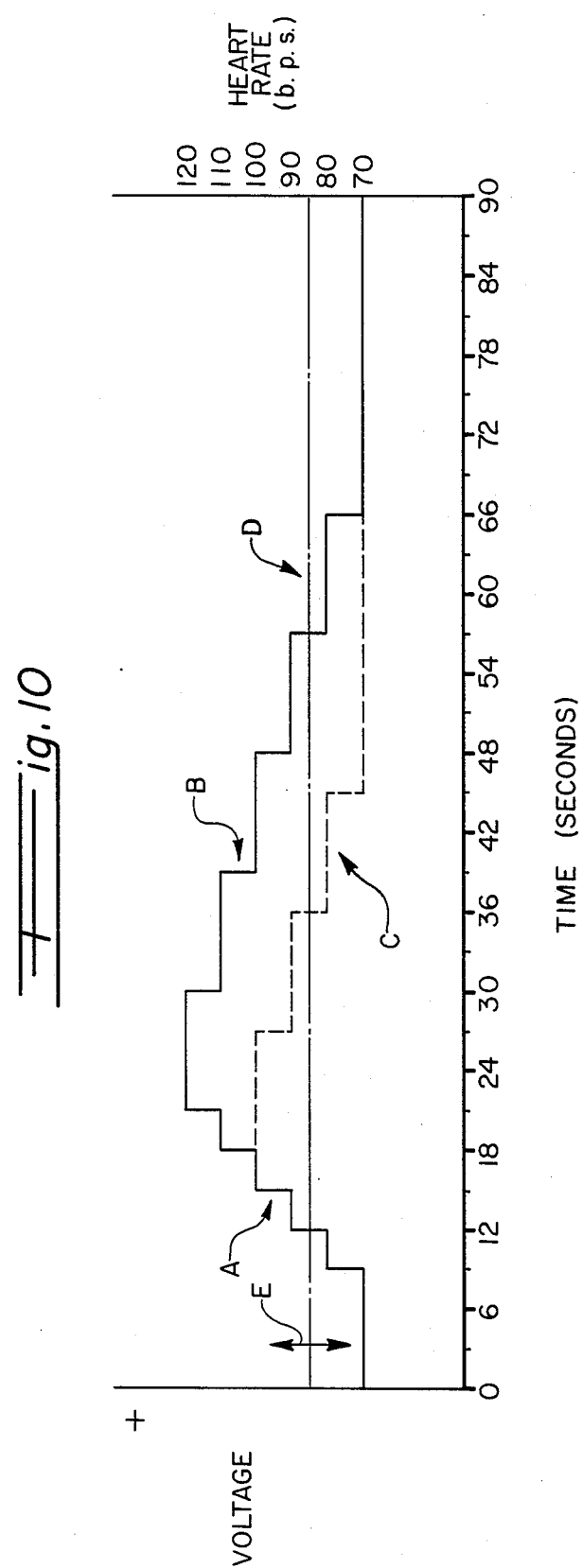

SYSTEM FOR AND METHOD OF THERAPEUTIC STIMULATION OF A PATIENT'S HEART

CROSS REFERENCE TO RELATED APPLICATION

This application is a continuation-in-part of U.S. patent application Ser. No. 105, 030 filed Oct. 6, 1987, and entitled "Hemodynamically Responsive System for and Method of Treating a Malfunctioning Heart", the disclosure of which is incorporated herein in its entirety by reference.

BACKGROUND OF THE INVENTION

1. Field of the Invention

This invention relates to a system for and method of pacing a malfunctioning heart and, more particularly, to such a system and method which effects pacing in response to sensing hemodynamic change at a site in the circulatory system of a patient. The invention provides for pacing of a malfunctioning heart and, more particularly, to varying the escape interval or rate of a pacemaker in response to a hemodynamic parameter.

2. Description of the Prior Art

In recent years, substantial progress has been made in pacemakers for treating various heart disorders and arrhythmias. Past efforts have resulted in the development of implantable electronic pacemakers which, in response to the detection of an abnormal cardiac condition, effect a restoration of cardiac rhythm by pacing.

External and implantable pacemakers for the therapeutic stimulation of the heart are well known in the art. Initially these cardiac pacers were asynchronous in operation providing stimulating pulses to the heart at a fixed rate independent of the physiological demand of the patient. Later demand pacemakers were developed as exemplified by U.S. Pat. No. 3,345,990 to Berkovitz. A further example of an early demand pacemaker is disclosed in U.S. Pat. No. 3,478,746 to Greatback. These disclosed devices provide stimulating pulses to the heart only in the absence of naturally occurring cardiac activity. This known form of pacing system permits the underlying cardiac rhythm of a patient to inhibit the pacemaker if the patient's intrinsic heart rate is above the preset escape interval of the pacing system. However, if the intrinsic cardiac activity of the patient drops below the minimum rate set by the escape interval of the pacing system, stimulating pulses will be supplied to the heart. In this fashion the demand pacemaker provides a lower boundary rate below which the patient's heart will not be permitted to drop.

Subsequently, more effective demand pacemakers of the hysteresis type were developed, an example being disclosed in the U.S. Pat. No. RE 28,003 to Gobeli. This hysteresis pacemaker permits the heart to inhibit the pacemaker down to a sentinel rate set by the hysteresis pacemaker. However, if no intrinsic cardiac activity is detected during the sentinel escape interval, the patient's heart will be stimulated at a nominal escape interval which is somewhat shorter than the lower hysteresis rate. In operation, the hysteresis pacemaker alters the escape interval in response to detected cardiac events.

More recently, pacemakers have been disclosed which rely upon a historical average of detected cardiac activity to set the escape interval. An example of one such pacer is disclosed in U.S. Pat. No. 3,921,642 to Preston.

Other forms of rate-adaptive pacemakers have also been proposed. These pacemakers rely on the sensing of atrial activity, blood pH, respiratory rate or QT interval data to alter the escape interval of the pacemaker. Discussions of some of these prior art proposals may be found in "Relation Between the QT Interval and Heart Rate", Rickards et al., Britt Heart J., 1981; 45; 56-61 and in "A Physiologically Controlled Cardiac Pacemaker", Krasner, Voukydis and Nardella, J.A.A.M.I, Volume I, No. 3, pgs. 14–20, 1966.

Recently, a pacemaker which alters the escape interval in response to the physiological demand or needs of the patient has been disclosed in U.S. Pat. No. 4,428,378 to Anderson et al. in which an activity sensor, mounted within an implanted pacemaker, detects the activity level of the patient and alters the escape interval between a preset minimum and maximum in response to the sensed activity level.

None of the above-mentioned prior art pacemakers involve the direct sensing of a hemodynamic parameter nor the concept of automatically adjusting the escape interval or rate of a pacemaker in response to changes in the sensed hemodynamic parameter.

A theoretical right atrial pressure feedback system to restore control of a rate-limited heart has been proposed in the publication of Todd J. Cohen, entitled "A Theoretical Right Atrial Pressure Feedback Heart Rate Control System to Restore Physiologic Control to a Rate-Limited Heart", Pace, Vol. 7, pgs. 671-677, July-August 1984. The disclosed system involves comparing a signal corresponding to right atrial pressure, as sensed by a feedback sensor, with a fixed signal corresponding to a command right atrial pressure. The comparison develops an error signal which, after processing, is used to control the impulse frequency of a pacemaker.

An implantable pacemaker pacing a heart in accordance with the heart rate needed to produce a required cardiac output in which a sensor is used to sense right ventricular systolic pressure is disclosed in the U.S. Pat. No. 4,566,456 to Koning et al. A microprocessor is provided to relate right ventricular pressure and/or the time derivative thereof with the rate needed to produce a desired cardiac output and to cause the pacemaker to pace the heart and, thus, produce the desired output when the heart is not naturally paced.

Neither the theoretical system of Cohen, supra, nor the system disclosed in the patent of Koning et al., supra, involves the sensing of a long term baseline pressure and its comparison with a short term current pressure to develop a signal for varying either the rate or escape interval of a pacemaker.

SUMMARY OF THE INVENTION

The principal object of the present invention is to provide a method of and a system for therapeutic stimulation of a patient's heart by adjusting the escape interval or rate of a pacemaker to effect pacing based at least partially on a sensed hemodynamic pressure at a site in the circulatory system of a patient.

Another object of the present invention is to provide an implantable system for therapeutic stimulation of a patient's heart by adjusting the escape interval of a demand pacemaker to effect pacing based at least partially on a sensed hemodynamic pressure at a site in the circulatory system of a patient.

A further object of the present invention is to provide a method of and a system for therapeutic stimulation of a patient's heart by pacing the heart which are, at least in part, hemodynamically responsive to change in current pressure from a long term sensed variable baseline mean pressure at a site in the circulatory system of a patient.

An additional object of the present invention is to provide a method of and a system for therapeutic stimulation of a patient's heart by pacing the heart which are, at least in part, hemodynamically responsive to change of short term (current) mean pressure from a long term baseline mean pressure.

From one vantage point, the present invention in its system aspect, can be seen as being in a system for therapeutic stimulation of a patient's heart, which includes means for varying the escape interval or the rate of a means for producing pacing pulses. Pressure responsive means sense pressure at a site in the circulatory system of a patient. Means responsive to output from the sensing means develop a variable first signal (baseline signal) representative of variable baseline mean pressure over a period of predetermined duration. Means responsive to output from the sensing means develop a second signal (current signal) representing current mean pressure over a period of given duration less than the period of predetermined duration. Control signal producing means responsive to the first signal and to the second signal develop a control signal upon the first signal and the second signal differing by at least a predetermined amount. Control means responsive to the control signal control the means for varying the escape interval or rate of the means for producing pacing pulses.

In a variant of the above-noted first system aspect, the present invention can be seen as being in a system for therapeutic stimulation of a patient's heart which includes a storage function and includes means for varying escape interval or rate of a means for producing pacing pulses. Means are provided for sensing pressure at a site in the circulatory system of a patient. Means responsive to output from the sensing means develop a variable first signal representative of mean pressure at the site over a period of predetermined duration. Means responsive to output from the sensing means develop a variable second signal representing mean pressure at the site over a period of given duration less than the period of predetermined duration. Means responsive to the variable first signal and to the variable second signal develop a stored first signal upon the first signal and the second signal differing by at least a predetermined amount. Means responsive to the stored first signal and to the second signal develop a control signal upon the stored first signal and the second signal differing by at least a given amount, which preferably is less than the predetermined amount. Means responsive to the control signal control the means for varying the escape interval or rate of the means for producing pacing pulses.

From another viewpoint, the present invention in its system aspect, can be seen as being in a system for therapeutic stimulation of a patient's heart, which includes means for varying the escape interval or the rate of a means for producing pacing pulses which is conjointly controlled. Pressure responsive means are provided for sensing pressure at a site in the circulatory system of a patient. Means responsive to output from the sensing means develop a variable first signal (baseline signal) representative of variable baseline mean pressure over a period of predetermined duration. Means responsive to output from the sensing means develop a second signal (current signal) representative of current mean pressure over a period of given duration less than the period of predetermined duration. Signal producing means responsive to the first signal and to the second signal develop a first control signal whenever the first signal and the second signal differ by at least a predetermined amount. Signal producing means responsive to a signal dependent on at least one physiological variable (for example, activity level of the patient) develop a second control signal. Control means contemporaneously responsive to the first control signal and to the second control signal conjointly control the means for producing pacing pulses for modifying the escape interval or rate thereof. Thus, the escape interval or rate may be controlled contemporaneously by the at least one physiological variable and by hemodynamic pressure at the site in the circulatory system.

A variant of the present invention in a second system aspect can be seen as being in a system for therapeutic stimulation of a patient's heart and which includes means for varying escape interval or rate of a means for producing pacing pulses and includes a storage function. Means sense pressure at a site in the circulatory system of a patient. Means responsive to output from the sensing means develop a variable first signal representative of mean pressure at the site over a period of predetermined duration. Means responsive to output from the sensing means develop a variable second signal representative of mean pressure at the site over a period of given duration less than the period of predetermined duration. Means respond to the variable first signal and to the variable second signal to develop a stored first signal upon the first signal and the second signal differing by at least a predetermined amount. Means respond to the first signal and to the second signal and develop a first control signal whenever the stored first signal and the second signal differ by at least a given amount, which preferably is less than the predetermined amount. Means responsive to a signal dependent on at least one physiological variable (such as activity level) develop a second control signal. Means contemporaneously responsive to the first control signal and to the second control signal conjointly control the means for producing pacing pulses for modifying the escape interval or rate thereof. Thus, the escape interval or rate may be controlled contemporaneously by the at least the one physiological variable, such as activity level, and by hemodynamic pressure at a site in the circulatory system.

From another vantage point, the present invention in its system aspect, can be considered as being in a system for therapeutic stimulation of a patient's heart, which includes means for varying escape interval or rate of a means for producing pacing pulses which is alternatively controlled. Pressure responsive means sense pressure at a site in circulatory system of a patient. Means responsive to output from the sensing means develop a variable first signal (baseline signal) representative of variable baseline mean pressure over a period of predetermined duration Means responsive to output from the sensing means develop a second signal (current signal) representative of current mean pressure over a period of given duration less than the period of predetermined duration. Signal means responsive to the first signal and to the second signal develop a first control signal whenever the first signal and the second signal differ by at least a predetermined amount. Signal producing means responsive to a signal dependent on at least one physiological variable (for example, activity level of the patient) develop a second control signal. Means alternatively supply either the first control signal or the second control signal to the means for varying the escape interval or rate of the means for producing pacing pulses, the second control signal being supplied in absence of the first control signal and the first control signal being supplied when present to exclusion of the second control signal. Thus, the escape interval or rate may be controlled alternatively by the at least one physiological variable and the hemodynamic pressure at the site in the circulatory system.

A variant of the third exemplary embodiment of the present invention, in its system aspect, also involves the storage function in a system for therapeutic stimulation of a patient's heart which includes means for varying escape interval or rate of a means for producing pacing pulses. Means is provided for sensing pressure at a site in circulatory system of a patient. Means responsive to output from the sensing mean develop a variable first signal representative of means pressure at the site over a period of predetermined duration. Means responsive to output from the sensing means develop a variable second signal representative of mean pressure at the site over a period of given duration less than the period of predetermined duration. Means respond to the first signal and to the second signal to develop a stored first signal upon the first signal and the second signal differing by at least a predetermined amount. Means responsive to the stored first signal and to the second signal develop a first control signal whenever the first signal and the second signal differ by at least a given amount, which preferably is less than the predetermined amount. Means responsive to a signal dependent on at least one physiological variable develop a second control signal. Means are provided for alternatively supplying either the first control signal or the second control signal to the means for varying the escape interval or rate of the means for producing pacing pulses. The second control signal is supplied in absence of the first control signal, the first control signal being supplied, when present, to exclusion of the second control signal. Thus, the escape interval or rate may be controlled alternatively by the at least one physiological variable, such as activity level, and the hemodynamic pressure at a site in the circulatory system.

The second control signal can be derived from output from a piezoelectric force sensor or the like which converts vibrational energy at a pacemaker site into an activity level signal.

The means for sensing pressure at a site in a circulatory system may be constituted by means for sensing right atrial pressure, means for sensing right ventricular pressure, means for sensing central venous pressure, means for sensing left atrial pressure, means for sensing left ventricular pressure or means for sensing arterial pressure.

The system may include microprocessor means for developing the control signal or signals.

In its method aspect, the present invention can be seen as a method of therapeutic stimulation of a patient's heart which includes sensing pressure at a site in circulation system of a patient, and comparing variable mean sensed pressure (variable baseline mean pressure) as determined over a period of predetermined duration with mean sensed pressure (current mean pressure) as determined over a current period of given duration less than the duration of the period of predetermined duration to find if the determined mean pressures differ by at least a predetermined amount The invention provides the step of controlling the escape interval or rate of a pacing system whenever the mean pressures over the predetermined and given periods differ by at least a predetermined amount.

The invention can also be seen, in its method aspect as a method of therapeutic stimulation of a patient's heart based conjointly on two sensed parameters. The method involves sensing pressure (the first parameter) at a site in circulatory system of a patient, and comparing variable mean sensed pressure (variable baseline mean pressure) at the site as determined over a period of predetermined duration with mean sensed pressure (current mean pressure) at the site as determined over a current period of given duration less than the duration of the period of predetermined duration to find if the determined mean pressures differ by at least a predetermined amount. The method also involves sensing at least one activity related physiological variable (the second parameter) of the patient, and controlling the escape interval or the rate rate of a pacing system contemporaneously based on the physiological variable and on the determined mean pressures.

From a different vantage point, the present invention in its method aspect, can be seen as a method of therapeutic stimulation of a patient's heart based alternately on two sensed parameters. The invention involves sensing pressure (the first parameter) at a site in circulatory system of a patient, and comparing variable mean sensed pressure (variable baseline mean pressure) at the site as determined over a period of predetermined duration with mean sensed pressure (current mean pressure) at the site as determined over a current period of given duration less than the duration of the period of predetermined duration to find if the determined mean pressures differ by at least a predetermined amount. The invention also involves sensing at least one activity related physiological variable (the second parameter) of the patient, and controlling the escape interval or the rate of a pacing system alternatively based on the physiological variable, whenever the determined mean pressures differ by less than the given amount, or based on pressure whenever the mean pressures differ by greater than the given amount, to the exclusion of the activity level of the patient.

In its method aspects, the present invention may preferably be realized by storing a representation of the mean sensed pressure at the site as determined over the period of predetermined duration at the time the mean pressures at the site differed by the at least predetermined amount. Thereafter, the current mean pressure is compared with the stored representations and the escape interval or rate controlled so long as these differ by at least the predetermined amount or slightly less.

The step of sensing pressure may be constituted by sensing right atrial pressure, by sensing right ventricular pressure, by sensing central venous pressure, by sensing left atrial pressure, by sensing left ventricular pressure, or by sensing arterial pressure.

BRIEF DESCRIPTION OF THE DRAWINGS

The novel features that are considered characteristic of the invention are set forth with particularity in the appended claims. The invention itself, however, both as to its organization and its method of operation, together with other objects and advantages thereof is to be understood from the following description of illustrative embodiments, when read in conjunction with the accompanying drawings.

FIG. 2A is an illustration of one catheter, which may be used in practicing the present invention, positioned within a heart, a pressure responsive sensor forming part of the catheter being shown positioned inside the right ventricle.

FIG. 2B is an illustration of a second catheter, which may be used in practicing the present invention, positioned within a heart, a pressure responsive sensor forming part of the catheter being shown positioned within the right atrium.

FIG. 2C is an illustration of a third catheter, which may be used in practicing the present invention, positioned within the right side of the heart, a pressure responsive sensor being shown positioned within a major vein feeding into the superior vena cava.

FIG. 2D is an illustration of a fourth catheter, which may be used in practicing the present invention, positioned within the right side of the heart, a pressure responsive sensor being shown positioned within the left ventricle.

FIG. 2E is an illustration of the fourth catheter positioned within the right side of the heart, a pressure responsive sensor being shown positioned within the left atrium.

FIG. 2F is an illustration of the fourth catheter positioned within the right side of the heart, a pressure responsive sensor being shown positioned at a point in the arterial system.

FIG. 10 is a graphic representation of the voltage output from the variable voltage source in the system embodiments of the present invention which is useful in understanding the operation of the systems.

DETAILED DESCRIPTION OF THE PREFERRED EMBODIMENTS

Figure 1:
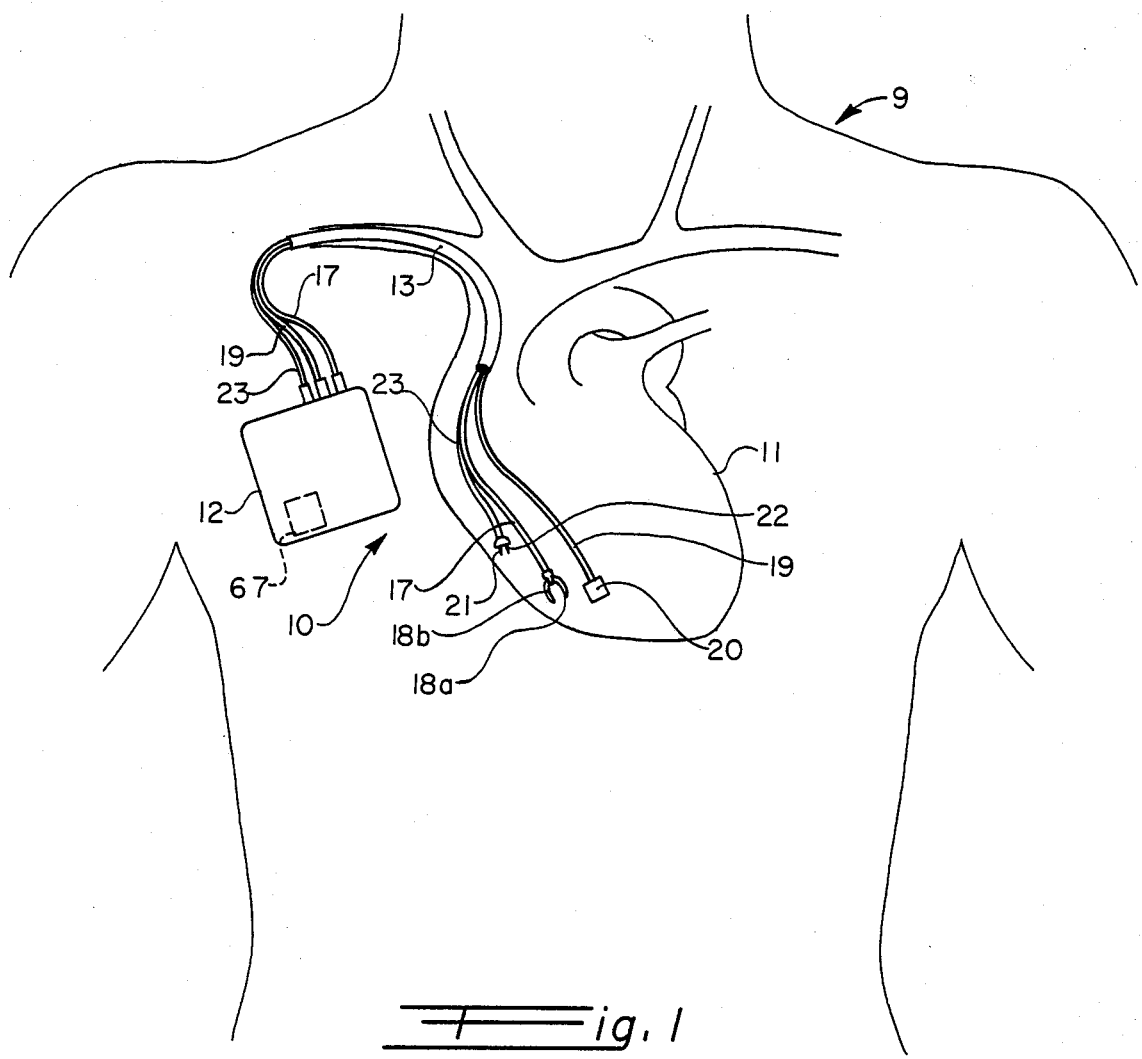
FIG. 1 is a diagrammatic, generalized illustration of an exemplary, implanted hemodynamically responsive system for pacing a malfunctioning heart in accordance with the present invention.

As shown in FIG. 1, an exemplary embodiment of an automatic implantable pacing system is designated generally by the numeral 10 and illustrated diagrammatically as being implanted within a human subject 9 having a heart 11. The pacing system 10 includes, as illustrated, an implanted housing 12 within which major circuit components of the system are housed. The size of the housing 12 may be approximately ¼ inch thick, 1½ inches wide and 1½ inches long. A pair of rate sensing electrodes 18a and 18b are provided within the heart 11, these electrodes being positioned in tissue and being conductively coupled to circuitry within the housing 12 via an insulated cable 17 which is positioned within a sheath 13 along its intermediate extent. The housing 12, as illustrated, is implanted outside the rib cage of the patient 9 on his or her right chest beneath the pectorous, as is conventional. A further pair of leads extend from a pressure responsive pressure-to-voltage transducer 20 positioned within the heart 11 to circuitry within the housing 12 via an insulated cable 19 which is, like the insulated cable 17, positioned within the sheath 13 along its intermediate extent.

Pacemaking circuitry within the housing 12 is provided to produce pacing signals to a pair of bipolar pacing electrodes 21 and 22, illustrated as being fixed in tissue within the lower right-side of the heart, that is within the right ventricle. The pacing electrodes 21 and 22 are connected by respective conductive leads within a cable 23 which communicates with pacing circuitry within the housing 12. While the bipolar pacing electrodes 21 and 22 are illustrated as being connected into tissue defined by an interior surface of the right ventricle, it is to be understood that these electrodes could be positioned on other interior surfaces of other chambers the heart or on an exterior surface of the heart 11 adjacent one or another of its four chambers, depending on the particular patient and his or her condition and the malfunction sought to be overcome. While the electrodes 21 and 22 are illustrated as being bipolar electrodes, for purpose of illustration, these electrodes could be configured as a unipolar electrode arrangement. As shown, single chamber pacing is provided; however, it is to be understood that the present invention can be applied to dual chamber pacing systems using either the bipolar or unipolar variants.

In some embodiments of the system (FIGS. 5, 7 and 9), an activity level sensor 67, indicated generally in FIG. 1 by the numeral is positioned within the implanted housing 12 for the purpose of developing a signal representing the current level of physical activity of the patient. A parameter other than the kinetic activity level of the patient may be used in practicing the present invention in either its system or method aspects; among these parameters are pH, respiration rate, Q-T interval, body temperature, blood temperature, lactic acid level, systolic time interval, pre-ejection interval or period, perspiration change, $CO_2$ level in the patient's blood, CO level in the patient's $O_2$ level in the patient's blood and the like. In such cases, a sensor or transducer for such parameters would replace the sensor 67 and would be appropriately positioned in or on the patient in a conventional manner.

It is to be understood that the insulated cable 17 (or the pair of leads therein), the insulated cable 23 (or the pair of leads therein) and the insulated cable 19 (or the pair of leads therein) can all be incorporated into a single cable, the rate sensing electrodes 18a and 18b, the pacing electrodes 21 and 23 and the pressure transducer 20 being carried by and forming parts of a single catheter.

Turning to FIG. 2A, a more detailed illustration of the heart 11 of a subject, shows the heart in somewhat more detail and in section so that placement of parts of the system within the heart 11 can be seen in more detail, albeit diagrammatically. The heart 11 as illustrated includes a right ventricle 26, a right atrium 27, a left atrium 28 and a left ventricle 30. The pacing electrodes 21 and 22 are shown as being positioned on the interior wall of right ventricle 26 for the purpose of illustration; these pacing electrodes could be placed elsewhere on or within the heart 11, as noted above, in accordance with the needs of individual patients, taking into account the best particular location most suitable for correcting or overcoming the particular malfunction involved, the condition of the 15 individual patient and his or her heart being taken into account. If desired, the invention can be adapted to systems in which the pacing and rate-sensing functions are provided by the same electrodes.

Heart rate wave (R-wave) sensing electrodes 18a and 18b are illustrated as being positioned near the apex of the heart 11 within the right ventricle 26, for purposes of illustration. Other locations are equally well suited; again, the selected location being chosen with the condition of the particular patient and his or her heart in mind. The electrodes 18a and 18b are conductively connected to the circuitry within the housing 12 (FIG. 1) via a pair leads within the cable 17. The cables 17, 19 and 23 are sheathed within the sheath 13 which extends out of the venous system of the patient to the implanted pacemaker circuitry within the housing 12.

The pressure-to-voltage transducer 20, as illustrated in FIG. 2A, is positioned within the right ventricle 26, a site in a patient's circulatory system. Two conductive leads 19a and 19b within the cable provide electrical communication from the pressure responsive transducer 20 to circuitry within the housing 12 (FIG. 1). Thus, a D.C. voltage signal representative of the actual, instant pressure within the right ventricle 26 is fed to the circuitry within the implanted housing 12 (FIG. 1).

As illustrated in FIGS. 2B-2F, the heart 11, as well as the components of the system of the present invention, other than the pressure-to-voltage transducer 20, correspond to the heart 11 and the system components as shown in FIG. 2A. The placement of the transducer 20 differs, in each of FIGS. 2B-2F. As shown in FIG. 2A, the transducer 20 provides, as its output, a variable D.C. voltage representative of the varying pressure within the right ventricle 26. As shown respectively in FIGS. 2B-2F, the transducer 20 is illustrated as being positioned within other sites in a patient's circulatory system and produces a variable D.C. voltage which represents respectively the pressure within these other sites, namely, the right atrium 27, within the central venous system (in particular, a major vein 29), the left ventricle 30, the left atrium 28 and the arterial system (in particular, an artery 31 remote from the heart 11). In FIGS. 2A-2C the cables 17 and 19 are positioned within the sheath 13. In FIGS. 2D-2F, the cable 18 is illustrated within the sheath 13, while the cable 19 is not so positioned, exiting the circulatory system at points removed from the sheath 13. In all cases the cable 19 extends to the housing 12 (FIG. 1) and communicates with the circuitry therein, as does the cable 17.

Figure 3:
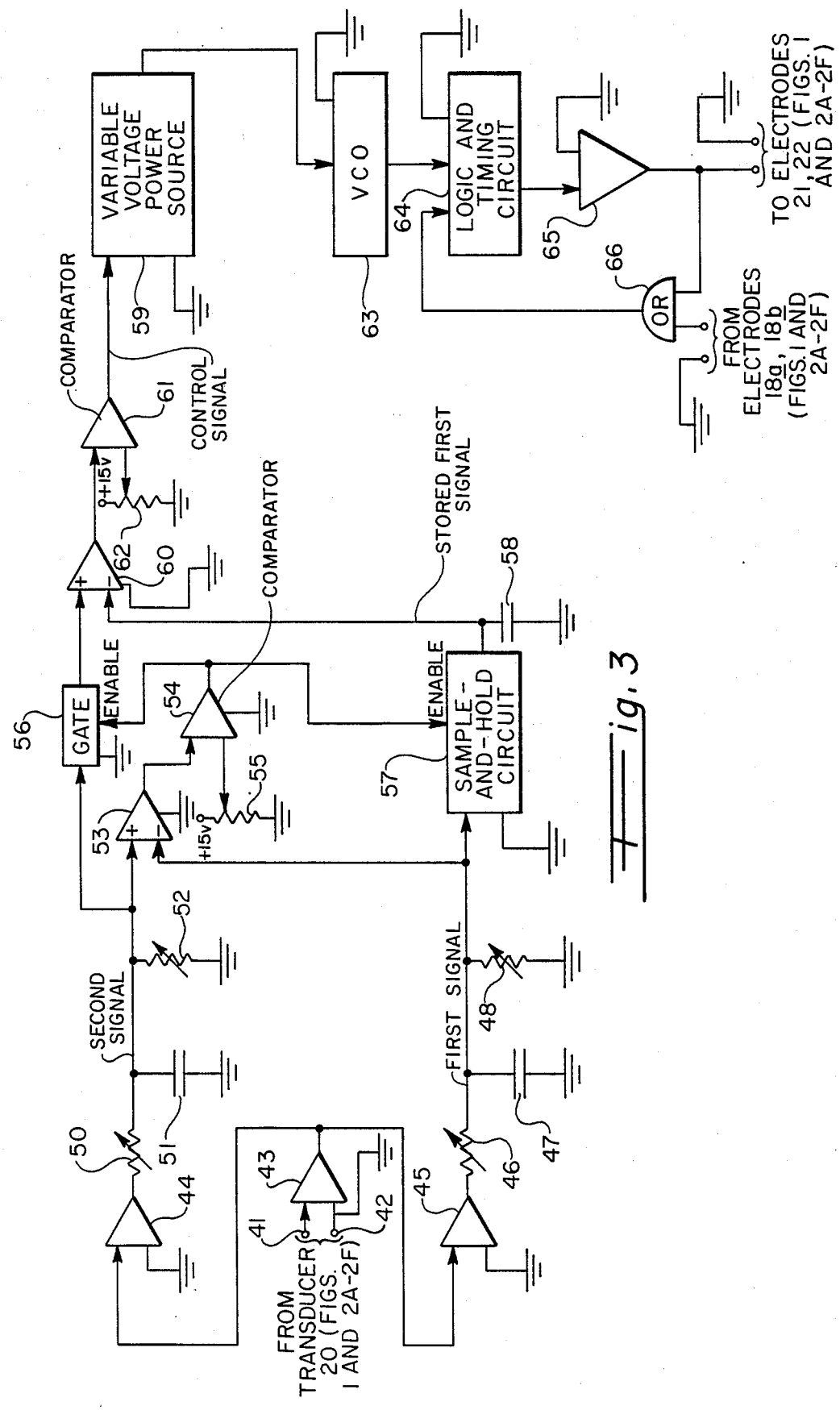
FIG. 3 is a partially block, schematic diagram of a hemodynamically responsive system for therapeutic stimulation of a patient's heart by pacing the malfunctioning heart in accordance with a first exemplary embodiment of the present invention which is pressure responsive and effects a change in the escape interval or rate.

Turning to FIG. 3, a first exemplary embodiment of the circuit components, which may be positioned within the implantable pacemaker housing 12 (FIG. 1), includes a pair of input terminals 41, 42 which receive the variable D.C. voltage output signal representing pressure from the pressure responsive transducer 20 (FIGS. 1, 2A-2F), the terminal 42 being connected to a point of circuit reference potential (ground). The terminals 41 and 42 are connected to an amplifier 43, which amplifies the pressure representing D.C. input signal from the transducer 20 and feeds the same to respective buffer amplifiers 44 and 45.

The output from the buffer amplifier 45 is supplied to an RC circuit constituted by an adjustable resistor 46 connected to ground via a series connected storage capacitor 47 having a large adjustable resistor 48 connected in parallel therewith. The time constants (charging and discharging) of these circuit components are such that the varying D.C. voltage (first signal) across the capacitor 47 represents the mean pressure sensed by the transducer 20 (FIGS. 1, 2A-2F) over a period of predetermined duration, a relatively long period, for example during the preceding fifteen (15) minutes or even longer (for example a number of hours) or shorter (for example one hundred twenty (120) seconds) being suitable in some cases. The first signal is thus, a variable baseline signal representing real-time baseline pressure at a site in the circulatory system of a patient. The resistors 46 and 48 may be set by a medical professional to suit the particular patient involved, so far as what the most suitable period length for baseline data acquisition appears to be most desirable for an individual patient. The varying D.C. voltage (first signal) across the capacitor 47 thus represents a long term mean baseline pressure, a varying baseline signal. The term "mean" as used herein is broad and includes the average value as well as values near the average. The output from the buffer amplifier 44 is supplied to a second RC circuit constituted by an adjustable resistor 50 connected to ground via a capacitor 51, which has an adjustable resistor 52 connected in parallel therewith. The time constants (charging and discharging) of these circuit components are such that the varying D.C. voltage (second signal) which appears across the capacitor 51 represents the short term mean pressure sensed by the transducer 20 (FIGS. 1, 2A-2F) over a period of given duration, a relatively short period, for example, during the preceding fifteen (15) seconds or longer (for example 60 seconds) or shorter (for example six seconds). The second signal is, thus, a varying current signal representing current pressure at a site in the circulatory system of a patient. The resistors 50 and 52 may be set by a medical professional to suit the particular patient involved, so far as what the most suitable period length for current data acquisition appears to be most desirable for the individual patient. Albeit, analogue circuits are illustrated, it is to be appreciated that the pressure could be monitored and digital signals derived. Moreover, mean systolic or diastolic pressures could be used as the parameter sensed and from which the baseline and current signals are derived in either the analogue or digital variants.

As illustrated the long term (baseline) and short term (current) varying D.C. voltage signals (the first signal and the second signal) which appear across the respective capacitors 47 and 51 are fed respectively to the inverting and noninverting terminals of an operational amplifier 53, a difference D.C. voltage signal appearing as the output from the operational amplifier 53. As shown, the inverting and noninverting terminals of the operational amplifier 53 are connected as they would be were pressures other than arterial pressures to be involved. Were MAP to be the hemodynamic parameter involved, the inverting and noninverting terminals of the amplifier 53 would be reversed. The D.C. output signal from the operational amplifier 53 is fed to a first input terminal of a first comparator 54, the second input terminal of the comparator 54 is connected to the wiper of a potentiometer 55 which is connected between ground and a point of fixed D.C. potential, illustrated as being +15 volts, from an internal power supply bus.

Whenever the voltage supplied to the comparator 54 from the operational amplifier 53 exceeds the voltage supplied via the wiper from the potentiometer 55, a low (ZERO) level on the output terminal from the comparator 54 goes high (ONE), the ONE signal being coupled as an enabling input to a gate 56 and to a sample-and-hold circuit 57 which receive, at their respective signal input terminals, the voltage (second signal) representing current mean pressure appearing across the capacitor 51 and the voltage (first signal) representing long term mean baseline pressure appearing across the capacitor 47.

A D.C. output (stored first signal) from the sample-and-hold circuit 57 is stored in a storage circuit, for the purpose of illustration shown as a capacitor 58. This stored voltage signal representing mean baseline (long-term) pressure for the predetermined period immediately preceding the instant of storage is supplied to the inverting input terminal of an operational amplifier 60 which has its noninverting input terminal connected to the output terminal of the gate 56 which, when enabled, passes the D.C. voltage (first signal) appearing across the capacitor 51 and representing varying current (short-term) mean pressure to the operational amplifier 60. As illustrated, the inverting and noninverting terminals of the operational amplifier 60 are shown as they would be connected were pressures other than arterial pressure involved. Were MAP to be the hemodynamic parameter selected to adjust the heart rate, the inverting and noninverting terminals of the operational amplifier 60 would be reversed. The output from the operational amplifier 60 is supplied to an input terminal of a comparator 61, which has its other input connected to the wiper of a potentiometer 62 connected between ground and the +15 volt power supply bus. It is to be understood that the wiper of the potentiometer 62 is set so that the difference required to produce a ONE output from the comparator 61 is less than the difference required to produce a ONE output from the comparator 54. In this way it is possible to avoid "cycling" of the system.

The voltage supplied to the comparator 61 from the operational amplifier 60 and the voltage supplied from the wiper of potentiometer 62 are compared. When the voltage from the operational amplifier 60 equals or exceeds the voltage appearing on the wiper of the potentiometer 62, the output from the comparator 61 goes from low (ZERO) to high (ONE) which is fed as a control signal to the control input of a variable voltage power supply 59. In operation, whenever the control input terminal of the variable voltage power source 59 goes from ZERO to ONE, its output voltage, which is used to control the pulse repetition rate (frequency) of a voltage controlled oscillator (VCO) 63, initially is caused to be increased in step fashion as illustrated in FIG. 10 by the solid line A, each step as shown corresponding to a heart rate increase of ten (10) beats per minute. As shown in FIG. 10, the step increases start from a given minimum default level (which as illustrated corresponds to a heart rate of 70 b.p.m.) and, in a maximum series of steps, illustrated as five steps of three seconds duration, provides an increasing rate up to a predetermined maximum rate, for example a rate of 120 b.p.m. as illustrated by the solid line A. In the event the output from the comparator 61 goes from ONE to ZERO, which would result were the difference between the stored first signal and the second signal to return to an acceptable level (reflecting an acceptable relationship between the long term mean pressure and the short term mean pressure). Before the predetermined maximum heart rate is achieved, the output from the variable voltage source 59 is no longer increased held for ten (10) seconds. In either case, after holding for a predetermined time, for example, ten seconds, the output voltage from the variable voltage source 59 is decreased, in step fashion, as illustrated in FIG. 10 both by a solid line B and by a dashed line C until the low default voltage level is achieved (corresponding to a heart rate of 70 b.p.m.). Each step is maintained for ten seconds until the minimum default level of 70 is achieved or, were the difference between long term and short term pressures to again become unacceptable, the routine of increasing the heart rate would again be initiated and again be decreased. It is possible that the heart rate would be controlled in such a fashion that the rate would continue to be increased and decreased in step fashion in the absence of achieving the default rate. The VCO 63 is operatively arranged to oscillate at a minimum rate in the absence of a ONE signal from the comparator 61 and provide an output to logic and timing circuitry 64 of the demand pacemaker for establishing the maximum escape interval which sets the minimum heart rate, for example a rate of 70 beats per second (b.p.s.) . As the control voltage level to the VCO 63 increases in step fashion, due to the comparison of the long term and short term mean pressures departing from one another by a predetermined amount, the escape interval is shortened thereby providing a higher pacing or heart rate. The pulse rate of the VCO 63 is increased and remains at the higher rates until the difference between the current mean pressure and the long term mean pressure (represented by the voltage stored by the sample-and-hold circuit 57) returns to normal at which time the output of the VCO 63 returns to its lowest rate in a series of ten beats per minute steps of ten second periods.

The output from the VCO 63 is supplied to a conventional logic and timing circuitry 64 (of the type used in the rate adaptive pacemaker disclosed in the U.S. Pat.

No. 4,428,378, supra) which, in turn, supplies its output pulses to a pacing amplifier 65 which provides amplified individual pacing output pulses to the pacing electrodes 21 and 22 (FIG. 1 or FIGS. 2A–2F) provided a pulse from the R-wave sensing electrodes 18a, 18b (FIG. 1) or the R-wave sensing electrodes 18a, 18b (FIGS. 2A–2F) have not been supplied to the logic and timing circuit 64 via an OR gate 66 to inhibit its output to the amplifier 65 in the event a normal heart beat occurs before expiration of the escape interval then in force. Thus, the system has the natural of a demand pacing system controlled by hemodynamic pressure conditions in accordance with the present invention. The other input of the OR gate 66 is supplied from the output terminal of the pacing amplifier 65. Thus, the escape interval is reset in the logic and timing circuitry 64 whenever a pulse is supplied to the OR gate 66 from either the amplifier 65 or from the rate sensing electrodes 18a, 18b.

The system illustrated in FIG. 3 can be used to carry out a first, exemplary method embodiment of the present invention, a method of therapeutic stimulation of a patient's heart comprising: sensing pressure at a site in circulation system of a 15 patient, comparing mean sensed pressure at the site as determined over a period of predetermined duration with mean sensed pressure at the site as determined over a current period of given duration less than the duration of the period of predetermined duration to find if the determined mean pressures at the site differ by at least a predetermined amount, and controlling escape interval or rate of a pacing system whenever the mean pressures differ by at least the predetermined amount. More particularly, the first exemplary embodiment of the present invention, in its method aspect, is as illustrated in the flow chart shown in FIG. 4.

Figure 5:
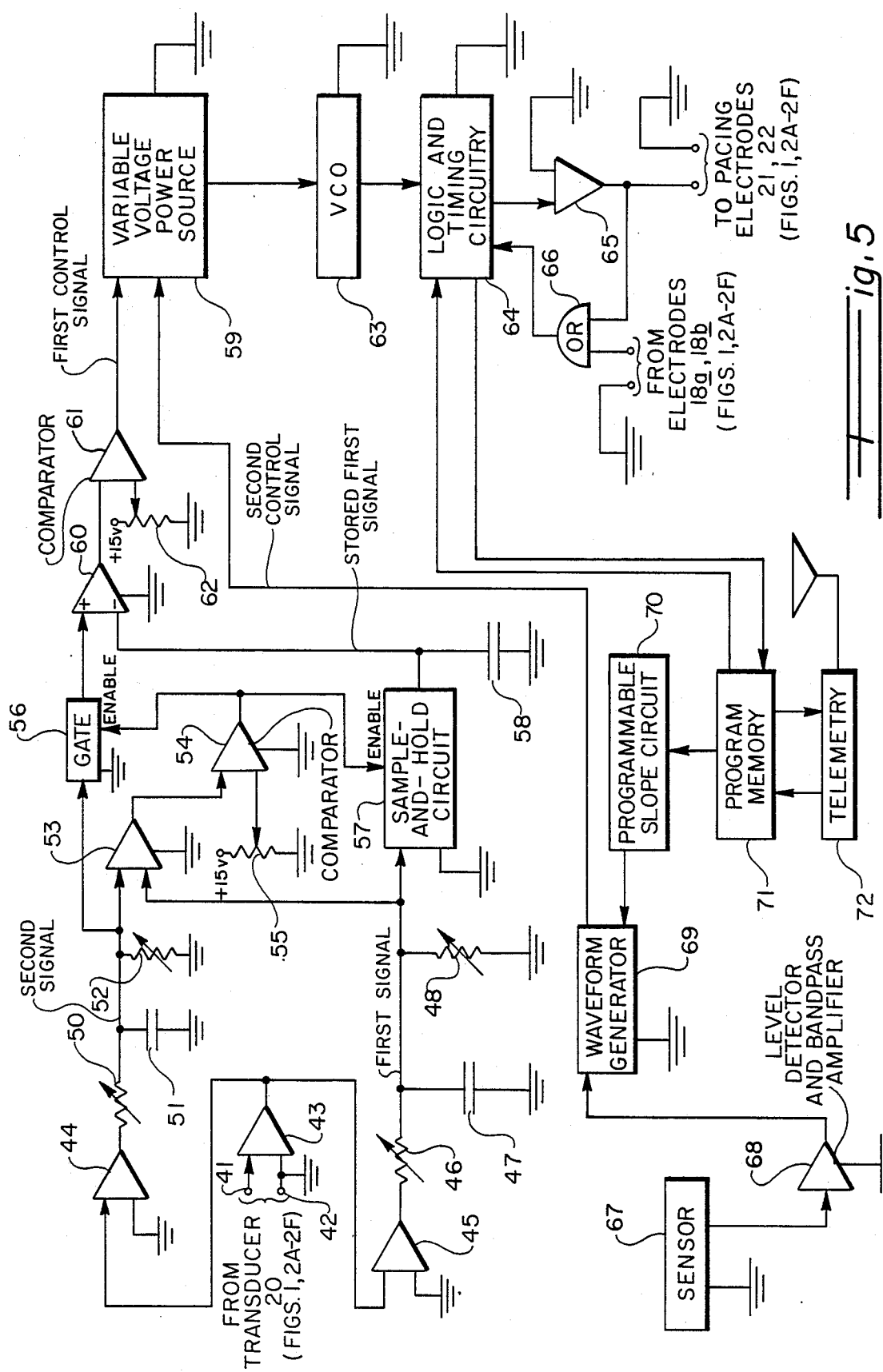
FIG. 5 is a partially block, schematic diagram of a hemodynamically responsive system for therapeutic stimulation of a patient's heart by pacing the malfunctioning heart in accordance with a second exemplary embodiment of the present invention which is contemporaneously and conjointly pressure and activity level responsive, and effects a change in the escape interval or rate.

Turning to FIG. 5, a second exemplary embodiment of the circuit components, which may be positioned within the implantable pacemaker housing 12 (FIG. 1), includes a pair of input terminals 41, 42 which receive the variable D.C. voltage output signal representing pressure from the pressure responsive transducer 20 (FIGS. 1, 2A–2F), the terminal 42 being connected to a point of circuit reference potential (ground). The terminals 41 and 42 are connected to an amplifier 43, which amplifies the pressure representing D.C. input signal from the transducer 20 and feeds the same to respective buffer amplifiers 44 and 45.

The output from the buffer amplifier 45 is supplied to an RC circuit constituted by an adjustable resistor 46 connected to ground via a series connected storage capacitor 47 having a large adjustable resistor 48 connected in parallel therewith. The time constants (charging and discharging) of these circuit components are such that the varying D.C. voltage (first signal) across the capacitor 47 represents the mean pressure sensed by the transducer 20 (FIGS. 1, 2A–2F) over a period of predetermined duration, a relatively long period, for example during the preceding fifteen (15) minutes or even longer (for example a number of hours) or shorter (for example one hundred twenty (120) seconds) being suitable in some cases. The first signal is, thus, a variable baseline signal representing real time baseline pressure at a site in the circulatory system of a patient. The resistors 46 and 48 may be set by a medical professional to suit the particular patient involved, so far as what the most suitable period length for baseline data acquisition appears to be most desirable for an individual patient. The varying D.C. voltage (first signal) across the capacitor 47 thus represents a long term mean baseline pressure, a varying baseline signal. The term "mean" as used herein is broad and includes the average value as well as values near the average. The output from the buffer amplifier 44 is supplied to a second RC circuit constituted by an adjustable resistor 50 connected to ground via a capacitor 51, which has an adjustable resistor 52 connected in parallel therewith. The time constants (charging and discharging) of these circuit components are such that the varying D.C. voltage (second signal) which appears across the capacitor 51 represents the short term mean pressure sensed by the transducer 20 (FIGS. 1, 2A–2F) over a period of given duration, a relatively short period, for example, during the preceding fifteen (15) seconds or longer (for example 60 seconds) or shorter (for example six seconds). The second signal is, thus, a varying current signal representing current pressure at a site in the circulatory system of a patient. The resistors 50 and 52 may be set by a medical professional to suit the particular patient involved, so far as what the most suitable period length for current data acquisition appears to be most desirable for the individual patient.

As illustrated the long term (baseline) and short term (current) varying D.C. voltage signals (the first signal and the second signal) which appear across the respective capacitors 47 and 51 are fed respectively to the inverting and noninverting terminals of an operational amplifier 53, a difference D.C. voltage signal appearing as the output from the operational amplifier 53. As shown, the inverting and noninverting terminals of the operational amplifier 53 are connected as they would be were pressures other than arterial pressures to be involved. Were MAP to be the hemodynamic parameter involved, the inverting and noninverting terminals of the amplifier 53 would be reversed. The D.C. output signal from the operational amplifier 53 is fed to a first input terminal of a first comparator 54, the second input terminal of the comparator 54 is connected to the wiper of a potentiometer 55 which is connected between ground and a point of fixed D.C. potential, illustrated as being +15 volts, from an internal power supply bus.

Whenever the voltage supplied to the comparator 54 from the operational amplifier 53 exceeds the voltage supplied via the wiper from the potentiometer 55, a low (ZERO) level on the output terminal from the comparator 54 goes high (ONE), the ONE signal being coupled as an enabling input to a gate 56 and to a sample-and-hold circuit 57 which receive, at their respective signal input terminals, the voltage (second signal) representing current mean pressure appearing across the capacitor 51 and the voltage (first signal) representing long term mean baseline pressure appearing across the capacitor 47.

A D.C. output (stored first signal) from the sample-and-hold circuit 57 is stored in a storage circuit, for the purpose of illustration shown as a capacitor 58. This stored voltage signal representing mean baseline (long-term) pressure for the predetermined period immediately preceding the instant of storage is supplied to the inverting input terminal of an operational amplifier 60 which has its noninverting input terminal connected to the output terminal of the gate 56, which when enabled, passes the D.C. voltage (first signal) appearing across the capacitor 51 and representing current (short-term) mean pressure to the operational amplifier 60. As illustrated, the inverting and noninverting terminals of the operational amplifier 60 are shown as they would be connected were pressures other than arterial pressure involved. Were MAP to be the hemodynamic parameter selected to adjust the escape interval or rate, the inverting and noninverting terminals would be reversed. The output from the operational amplifier 60 is supplied to an input terminal of a comparator 61, which has its other input connected to the wiper of a potentiometer 62 connected between ground and the +15 volt power supply bus. It is to be understood that the wiper of the potentiometer 62 is set so that the difference required to produce a ONE output from the comparator 61 is less than the difference required to produce a ONE output from the comparator 54. In this way it is possible to avoid "cycling" of the system.

The voltage supplied to the comparator 61 from the operational amplifier 60 and the voltage supplied from the wiper of potentiometer 62 are compared. When the voltage from the operational amplifier 60 equals or exceeds the voltage appearing on the wiper of the potentiometer 62, the output from the comparator 61 goes from low (ZERO) to high (ONE) which is fed as a first control signal to one of two control inputs of a variable voltage power supply 59. In operation, whenever the control input terminal of the variable voltage supply 59 goes from ZERO to ONE, its output voltage, which is used to control the pulse repetition rate (frequency) of a voltage controlled oscillator (VCO) 63, initially is caused to be increased in step fashion as shown in FIG. 10, each step as shown corresponding to a heart rate increase of ten (10) beats per minute. As shown, the step increases start from either a given default level (which corresponds to a heart rate of 70 b.p.m.) or a higher level (determined by the activity level or the like of the patient, as is to be described in more detail below and shown graphically by the dot-dash line D in FIG. 10) and, in a maximum series of steps, shown as five steps of three seconds duration provides an increasing rate up to a set maximum rate of, for example, 120 b.p.m. as shown in the solid line A. As illustrated by the dot-dash line 10, were the stepping to start from a level between steps, the initial step would be less than that required to produce a ten beat change, rather only that necessary to achieve the next step would take place. In the event the output from the comparator 61 goes from ONE to ZERO before the maximum rate is effected, the output from the power supply 59 is no longer increased in step fashion, but is held for ten (10) seconds as shown by the dashed line C. In either case, after holding for a predetermined time, for example, ten seconds, the output voltage from the variable voltage power supply 59 is decreased, in step fashion, as illustrated in FIG. 10 by a solid line B and a dashed line C until the low default voltage level is achieved (corresponding to a heart rate of 70 b.p.m.) or a somewhat higher level (corresponding to a heart rate of over 70 b.p.m. determined by the activity level), as illustrated by the dot-dash line D in FIG. 10 which rate may vary as diagrammatically illustrated by the double-arrowheaded line E depending on the activity level of the patient. The VCO 63 is operatively arranged to oscillate at a minimum pulse rate in the absence of any control voltage (first control signal) from the comparator 61 or an activity-related control voltage (second control signal) from a waveform generator 69 and provide an output to logic and timing circuitry 64 of the demand pacemaker for establishing the maximum escape interval which sets the minimum heart rate, for example a rate of 70 beats per second. As the control voltage level to the VCO 63 increases in step fashion, due to the comparison of the developed signals (first signal and second signal) representing the long term and short term mean pressures departing from one another, frequency of the VCO 63 is increased in step fashion and the escape interval is shortened thereby providing a higher pacing or heart rate. The pulse rate is increased and remains at the higher rates until the difference between the current mean pressure and the long term mean pressure, represented by the voltage (stored 15 first signal) stored by the sample-and-hold circuit 57, returns to normal at which time the output of the VCO 63 returns in step fashion either to its lowest rate or a somewhat higher rate determined by the output from the generator 69 in a series of ten beats per minute steps of ten second duration, the last step being somewhat less than a full step in the event the activity level of the patient dictates a higher rate.

The output from the VCO 63 is supplied to a conventional logic and timing circuitry 64 which, in turn, supplies its output pulses to a pacing amplifier 65 which provides amplified individual pacing output pulses to the pacing electrodes 21 and 22 (FIG. 1 or FIGS. 2A-2F provided a pulse from the R-wave sensing electrodes 18a, 18b (FIGS. 1, 2A-2F) has not been supplied to the logic and timing circuit 64 via an OR gate 66 to inhibit its output to the amplifier 65 in the event a normal heart beat occurs before expiration of the escape interval then in force. Thus, the system has the nature of a demand pacing system controlled jointly and contemporaneously by hemodynamic pressure conditions and an additional physiological parameter, for example, the activity level of the patient in accordance with the present invention. The other input of the OR gate 66 is supplied from the output terminal of the pacing amplifier 65. Thus, the escape interval is reset in the logic and timing circuitry 64 whenever a pulse is supplied to the OR gate 66 from either the amplifier 65 or from the rate sensing electrodes 18a, 18b.

As shown in FIG. 5, the system includes a piezoelectric force sensor 67 coupled to the hermetic enclosure of the implanted pacing system 10 (FIG. 1) for converting vibrational energy at the pacemaker site into a sensed activity signal. The sensed activity signal is applied to a bandpass amplifier 68 which rejects the low and high frequency components of the applied force. This signal is also level detected producing a processed activity signal which excludes low amplitude information within the designated passband of the bandpass amplifier 68. The processed activity signal produced by circuit amplifier 68 is supplied to a slow waveform generator 69 which integrates this activity over a selectable time period selected by programmable slope control circuit 70. The output of the slow waveform generator 69 is applied to the second control voltage input of the variable voltage power source 59 which feeds the controlled oscillator 63 converting the integrated activity signal into a variable basic pulse rate proportional to the magnitude of the activity parameter as possibly modified by the step voltage variation responsive to the above-mentioned hemodynamic pressure parameter. The activity related signal, as possibly modified by the hemodynamic related signal, is supplied to the logic and timing circuitry 64 as is conventional in demand pacemakers for altering the escape interval. The details of the implementation of the escape interval alteration circuitry is not provided since they are believed to be within the skill of pacemaker designers.

The escape interval may vary between an upper and lower bound which may, as illustrated, correspond respectively to a heart rate of 120 b.p.m. and 70 b.p.m. and may be noninvasively programmed through circuitry 72 and stored within the program memory 71 of the pacemaker. At the end of an escape interval an output stimulus is supplied to the heart through the pacing output amplifier 65 which is coupled to the patient's heart through a lead system to the pacing electrodes 21, 22 (FIGS. 1, 2A-2F). Likewise, sensed activity of the heart is detected from the R-wave sensing electrodes 18a, 18b (FIGS. 1, 2A-2F) and, if sensed, is supplied to the logic and timing circuitry 64 for resetting the escape interval in a known fashion. The escape interval is reset via the OR gate 66 which receives its inputs from the amplifier 65 or electrodes 18a, 18b Via the OR gate 66. An amplifier (not shown) may be provided between the one input to the OR circuit 66 from the electrodes 18a, 18b (FIGS. 1, 2A-2F). The programmable slope circuitry 70 receives slope parameter information through noninvasive programming of the system. The programmable slope circuit 70 controls how rapidly the pacemaker will move from a lower or preset minimum rate to its maximum or upper rate under the control of activity level related control signal. When the slope parameter is set at its highest value there will be large increases or changes in the rate of the pacemaker with the sensed activity of the patient while the pacemaker rate will change over a small range if this slope parameter is set at its lowest value. This, in essence, controls how rapidly the escape interval of the pacemaker will change in response to sensed activity. When the slope parameter is set at its highest value the pacemaker will respond quickly to the sensed activity of the patient while, when set at its lowest value, the pacemaker will respond slowly to the patient's activity. This parameter permits the physician to control the interaction of the pacemaker with the patient.

The system illustrated in FIG. 5 can be used to carry out a second, exemplary method embodiment of the present invention, a method of therapeutic stimulation of a patient's heart comprising: sensing pressure at a site in circulatory system of a patient, comparing mean pressure at the site as determined over a period of predetermined duration with mean pressure at the site as determined over a current period of given duration less than the duration of the period of predetermined duration to find if the determined mean pressures at the site differ by at least a predetermined amount, sensing at least one physiological variable (such as activity level) of the patient; and controlling escape interval or rate of a pacing system contemporaneously based on the physiological variable and on the determined mean pressures at the site.

Figure 6:
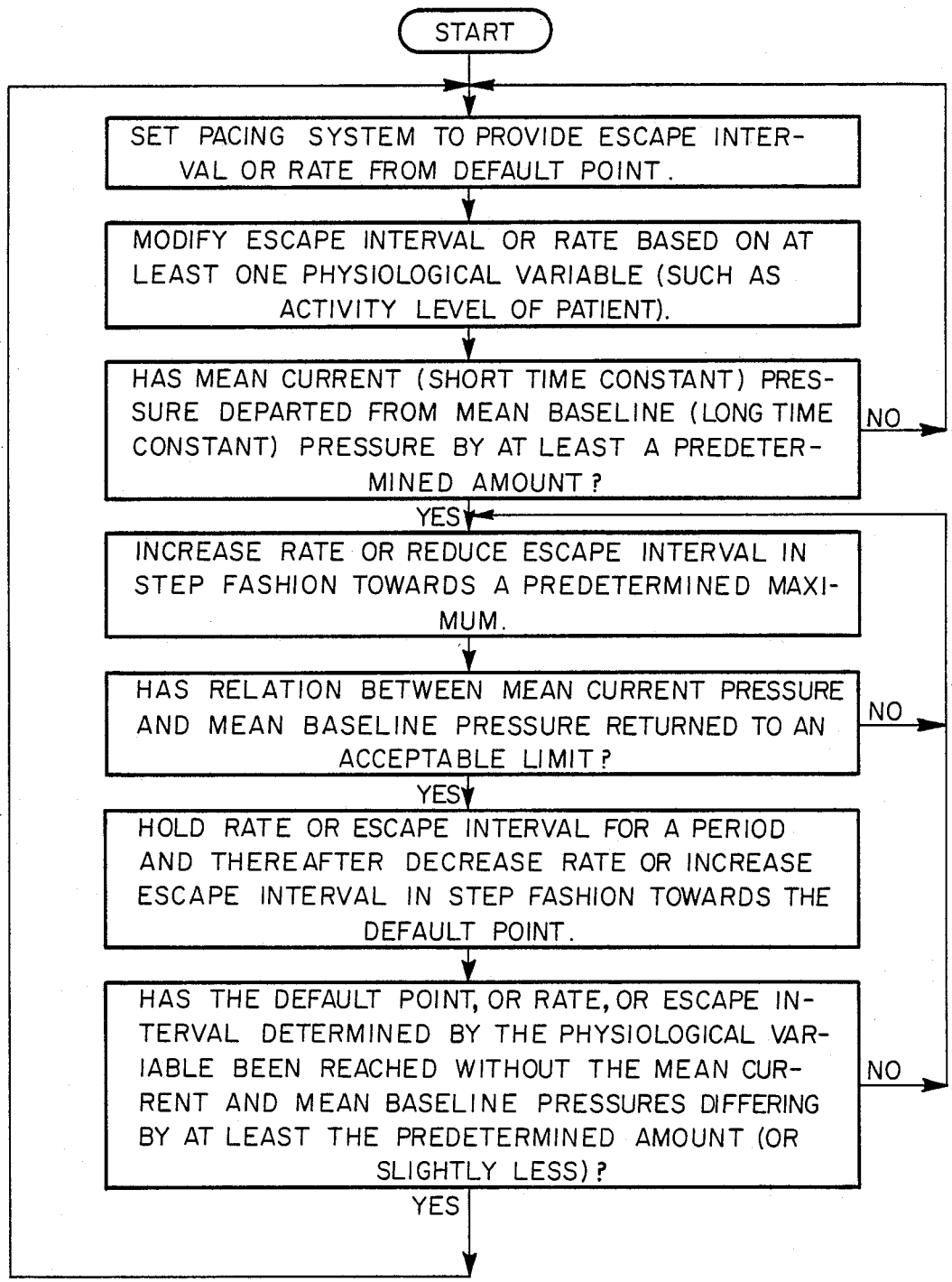
FIG. 6 constitutes a second exemplary flowchart of a series of actions or steps which may be carried out by the system of the present invention illustrated in FIG. 5 and effect achievement of the second embodiment of the invention in its method aspect.

More particularly, the second, method embodiment of the present invention may be viewed as a series of steps as illustrated in FIG. 6 in the form of a flow chart.

Figure 7:
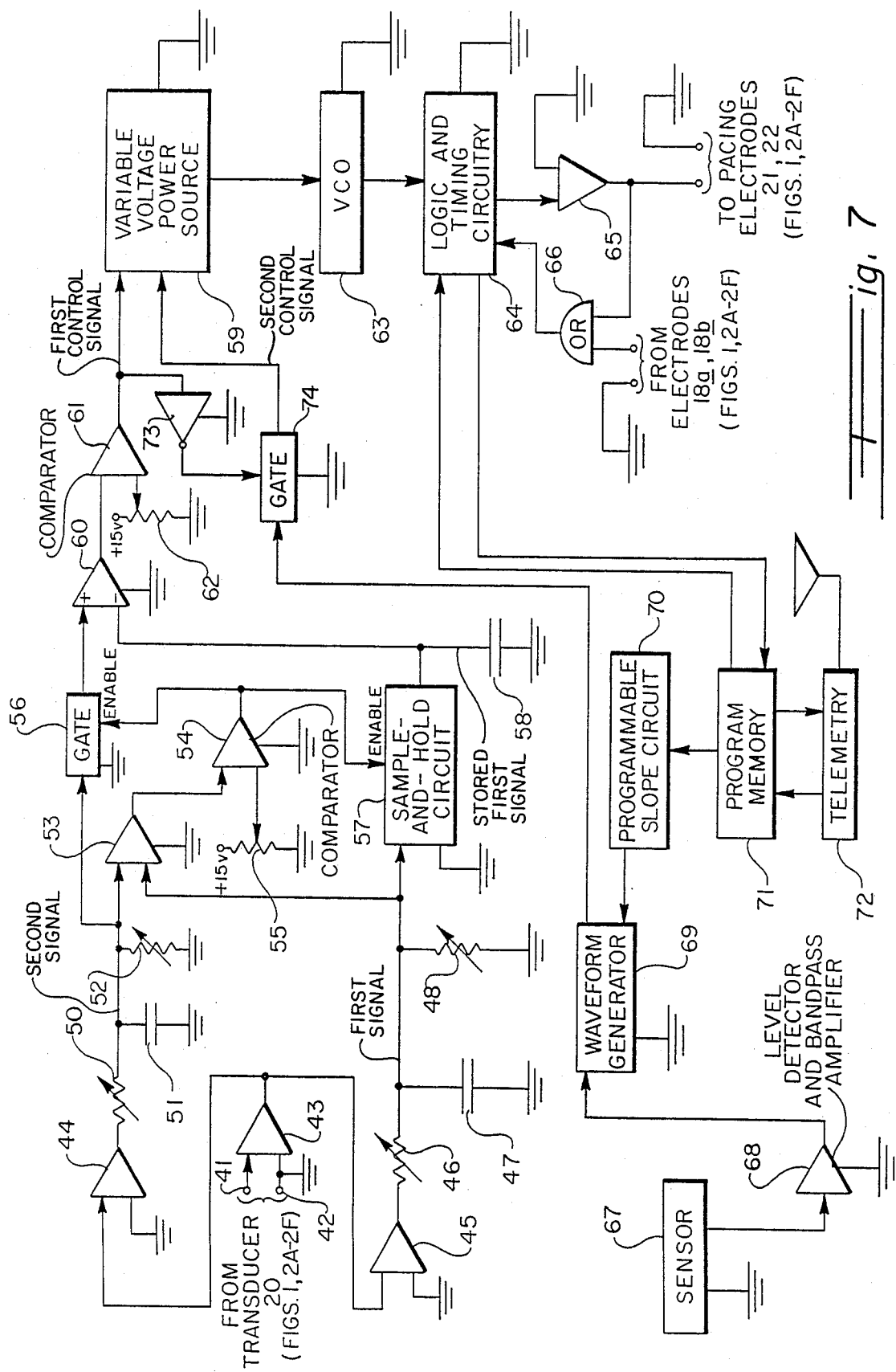
FIG. 7 is a partially block, schematic diagram of a hemodynamically responsive system for therapeutic stimulation of a patient's heart by pacing the malfunctioning heart in accordance with a third embodiment of the present invention which is, alternatively, pressure responsive or activity level responsive and effects a change in the escape interval or rate.

Turning to FIG. 7, a third exemplary embodiment of the circuit components, which may be positioned within the implantable pacemaker housing 12 (FIG. 1), includes a pair of input terminals 41, 42 which receive the variable D.C. voltage output signal representing pressure from the pressure responsive transducer 20 (FIGS. 1, 2A-2F), the terminal 42 being connected to a point of circuit reference potential (ground). The terminals 41 and 42 are connected to an amplifier 43, which amplifies the pressure representing D.C. input signal from the transducer 20 and feeds the same to respective buffer amplifiers 44 and 45.

The output from the buffer amplifier 45 is supplied to an RC circuit constituted by an adjustable resistor 46 connected to ground via a series connected storage capacitor 47 having a large adjustable resistor 48 connected in parallel therewith. The time constants (charging and discharging) of these circuit components are such that the varying D.C. voltage (first signal) across the capacitor 47 represents the mean pressure sensed by the transducer 20 (FIGS. 1, 2A-2F) over a period of predetermined duration, a relatively long period, for example during the preceding fifteen (15) minutes or even longer (for example a number of hours) or shorter (for example one hundred twenty (120) seconds) being suitable in some cases. The first signal is, thus, a variable baseline signal representing real time baseline pressure at a site in the circulatory system of a patient. The resistors 46 and 48 may be set by a medical professional to suit the particular patient involved, so far as what the most suitable period length for baseline data acquisition appears to be most desirable for an individual patient. The varying D.C. voltage (first signal) across the capacitor 47 thus represents a long term mean baseline pressure, a varying baseline signal. The term "mean" as used herein is broad and includes the average value as well as values near the average. The output from the buffer amplifier 44 is supplied to a second RC circuit constituted by an adjustable resistor 50 connected to ground via a capacitor 51, which has an adjustable resistor 52 connected in parallel therewith. The time constants (charging and discharging) of these circuit components are such that the varying D.C. voltage (second signal) which appears across the capacitor 51 represents the short term mean pressure sensed by the transducer 20 (FIGS. 1, 2A-2F) over a period of given duration, a relatively short period, for example, during the preceding fifteen (15) seconds or longer (for example 60 seconds) or shorter (for example six seconds). The second signal is, thus, a varying current signal representing current pressure at a site in the circulatory system of a patient. The resistors 50 and 52 may be set by a medical professional to suit the particular patient involved, so far as what the most suitable period length for current data acquisition appears to be most desirable for the individual patient.

As illustrated the long term (baseline) and short term (current) varying D.C. voltage signals (the first signal and the second signal) which appear across the respective capacitors 47 and 51 are fed respectively to the inverting and noninverting terminals of an operational amplifier 53, a difference D.C. voltage signal appearing as the output from the operational amplifier 53. As shown, the inverting and noninverting terminals of the operational amplifier 53 are connected as they would be were pressures other than arterial pressures to be involved. Were MAP to be the hemodynamic parameter involved, the inverting and noninverting terminals of the amplifier 53 would be reversed. The D.C. output signal from the operational amplifier 53 is fed to a first input terminal of a first comparator 54, the second input terminal of the comparator 54 is connected to the wiper of a potentiometer 55 which is connected between ground and a point of fixed D.C. potential, illustrated as being +15 volts, from an internal power supply bus. It is to be understood that the wiper of the potentiometer 62 is set so that the difference required to produce a ONE output from the comparator 61 is less than the difference required to produce a ONE output from the comparator 54. In this way it is possible to avoid "cycling" of the system.

Whenever the voltage supplied to the comparator 54 from the operational amplifier 53 exceeds the voltage supplied via the wiper from the potentiometer 55, a low (ZERO) level on the output terminal from the comparator 54 goes high (ONE), the ONE signal being coupled as an enabling input to a gate 56 and to a sample-and-hold circuit 57 which receive, at their respective signal input terminals, the voltage (second signal) representing current mean pressure appearing across the capacitor 51 and the voltage (first signal) representing long term mean baseline pressure appearing across the capacitor 47.

A D.C. output (stored first signal) from the sample-and-hold circuit 57 is stored in a storage circuit, for the purpose of illustration shown as a capacitor 58. This stored voltage signal representing mean baseline (long-term) pressure for the predetermined period immediately preceding the instant of storage is supplied to the inverting input terminal of an operational amplifier 60 which has its noninverting input terminal connected to the output terminal of the gate 56, which when enabled, passes the D.C. voltage (first signal) appearing across the capacitor 51 and representing current (short-term) mean pressure to the operational amplifier 60. As illustrated, the inverting and noninverting terminals of the operational amplifier 60 are shown as they would be connected were pressures other than arterial pressure involved. Were MAP to be the hemodynamic parameter selected to adjust the escape interval or rate, the inverting and noninverting terminals would be reversed. The output from the operational amplifier 60 is supplied to an input terminal of a comparator 61, which has its other input connected to the wiper of a potentiometer 62 connected between ground and the +15 volt power supply bus.

The voltage supplied to the comparator 61 from the operational amplifier 60 and the voltage supplied from the wiper of potentiometer 62 are compared. When the voltage from the operational amplifier 60 equals or exceeds the voltage appearing on the wiper of the potentiometer 62, the output from the comparator 61 goes from low (ZERO) to high (ONE) which is fed as a first control signal to one of two control inputs of a variable voltage power supply 59. In operation, whenever the control input terminal of the variable voltage supply 59 goes from ZERO to ONE, its output voltage, which is used to control the pulse repetition rate (frequency) of a voltage controlled oscillator (VCO) 63, initially is caused to be increased in step fashion as shown in FIG. 10, each step as shown corresponding to a heart rate increase of ten (10) beats per minute. As shown, the step increases start from either a given default level (which corresponds to a heart rate of 70 b.p.m.) or a higher level (determined by the activity level or the like of the patient, as is to be described in more detail below and shown graphically by the dot-dash line D in FIG. 10) and, in a maximum series of steps, shown as five steps of three seconds duration provides an increasing rate up to a set maximum rate of, for example, 120 b.p.m. shown in the solid line A. As illustrated by the dot-dash line 10, were the stepping to start from a level between steps, the initial step would be less than that required to produce a ten beat change, rather only that necessary to achieve the next step would take place. The first control signal is also fed to an inverter 73 which causes its output to turn a gate 74 off, removing the feed of a second control to the power source 59 from a waveform generator 69. Thus, control of the variable voltage power source 59 is preempted from the waveform generator 69 and turned over to the output from the comparator 61. In the event the output from the comparator 61 goes from ONE to ZERO before the maximum rate is effected, the output from the power supply 59 is no longer increased in step fashion, but is held for ten (10) seconds as shown by the dashed line C. In either case, after holding for a predetermined time, for example, ten seconds, the output voltage from the variable voltage power supply 59 is decreased, in step fashion, as illustrated in FIG. 10 by a solid line B and a dashed line C until the low default voltage level is achieved (corresponding to a heart rate of 70 b.p.m.) or a somewhat higher level (corresponding to a heart rate of over 70 b.p.m. determined by the activity level), as illustrated by the dot-dash line D in FIG. 10 which rate may vary as diagrammatically illustrated by the double-arrow-headed line E depending on the activity level of the patient. Thus, the control of the variable voltage power source 59 is returned to the waveform generator 69. The VCO 63 is operatively arranged to oscillate at a minimum pulse rate in the absence of any control voltage (first control signal) from the comparator 61 or an activity-related control voltage (second control signal) from a waveform generator 69 and provide an output to logic and timing circuitry 64 of the demand pacemaker for establishing the maximum escape interval which sets the minimum heart rate, for example a rate of 70 beats per second. As the control voltage level to the VCO 63 increases in step fashion, due to the comparison of the developed signals (first signal and second signal) representing the long term and short term mean pressures departing from one another, frequency of the VCO 63 is increased in step fashion and the escape interval is shortened thereby providing a higher pacing or heart rate. The pulse rate is increased and remains at the higher rates until the difference between the current mean pressure and the long term mean pressure, represented by the voltage (stored first signal) stored by the sample-and-hold circuit 57, returns to normal at which time the output of the VCO 63 returns in step fashion either to its lowest rate or a somewhat higher rate determined by the output from the generator 69 in a series of ten beats per minute steps of ten second duration, the last step being somewhat less than a full step in the event the activity level of the patient dictates a higher rate.

The output from the VCO 63 is supplied to a conventional logic and timing circuitry 64 which, in turn, supplies its output pulses to a pacing amplifier 65 which provides amplified individual pacing output pulses to the pacing electrodes 21 and 22 (FIG. 1 or FIGS. 2A–2F provided a pulse from the R-wave sensing electrodes 18a, 18b (FIGS. 1, 2A–2F) has not been supplied to the logic and timing circuit 64 via an OR gate 66 to inhibit its output to the amplifier 65 in the event a normal heart beat occurs before expiration of the escape interval then in force. Thus, the system illustrated in FIG. 7 has the nature of a demand pacing system controlled alternatively by hemodynamic pressure conditions and an additional physiological parameter, for example the activity level of the patient in accordance with the third embodiment of the present invention. The other input of the OR gate 66 is supplied from the output terminal of the pacing amplifier 65. Thus, the escape interval is reset in the logic and timing circuitry 64 whenever a pulse is supplied to the OR gate 66 from either the amplifier 65 or from the rate sensing electrodes 18a, 18b.

As shown in FIG. 7, the system includes a piezoelectric force sensor 67 coupled to the hermetic enclosure of the implanted pacing system 10 (FIG. 1) for converting vibrational energy at the pacemaker site into a sensed activity signal. The sensed activity signal is applied to a bandpass amplifier 68 which rejects the low and high frequency components of the applied force. This signal is also level detected producing a processed activity signal which excludes low amplitude information within the designated passband of the bandpass amplifier 68. The processed activity signal produced by circuit amplifier 68 is supplied to a slow waveform generator 69 which integrates this activity over a selectable time period selected by programmable slope control circuit 70. The output of the slow waveform generator 69 is applied, via the gate 74 in the absence of the first control signal from the comparator 61, to the second control voltage input of the variable voltage power source 59 which feeds the controlled oscillator 63 converting the integrated activity signal into a variable basic pulse rate proportional to the magnitude of the activity parameter as possibly modified by the step voltage variation responsive to the above-mentioned hemodynamic pressure parameter. The activity related signal, as possibly modified by the hemodynamic related signal, is supplied to the logic and timing circuitry 64 as is conventional demand pacemakers for altering the escape interval. The details of the implementation of the escape interval alteration circuitry is not provided singe they are believed to be within the skill of pacemaker designers.

The escape interval may vary between an upper and lower bound which may, as illustrated, correspond respectively to a heart rate of 120 b.p.m. and 72 b.p.m. and may be noninvasively programmed through telemetry circuitry 70 and stored within the program memory 71 of the pacemaker. At the end of an escape interval an output stimulus is supplied to the heart through the pacing output amplifier 65 which is coupled to the patient's heart through a lead system to the pacing electrodes 21, 22 (FIGS. 1, 2A-2F). Likewise, sensed activity of the heart is detected from the R-wave sensing electrodes 18a, 18b (FIGS. 1, 2A-2F) and, if sensed, is supplied to the logic and timing circuitry 64 for resetting the escape interval in a known fashion. The escape interval is reset via the OR gate 66 which receives its inputs from the amplifier 65 or electrodes 18a, 18b via the OR gate 66. An amplifier (not shown) may be provided between the one input to the OR circuit 66 from the electrodes 18a, 18b (FIGS. 1, 2A-2F). The programmable slope circuitry 70 receives slope parameter information through noninvasive programming of the system. The programmable slope circuit 70 controls how rapidly the pacemaker will move from a lower or preset minimum rate to its maximum or upper rate under the control of activity level related control signal. When the slope parameter is set at its highest value there will be large increases or changes in the rate of the pacemaker with the sensed activity of the patient while the pacemaker rate will change over a small range if this slope parameter is set at its lowest value. This, in essence, controls how rapidly the escape interval of the pacemaker will change in response to sensed activity. When the slope parameter is set at its highest value the pacemaker will respond quickly to the sensed activity of the patient while, when set at its lowest value, the pacemaker will respond slowly to the patient's activity. This parameter permits the physician to control the interaction of the pacemaker with the patient.

The third, exemplary embodiment of the present invention, in its method aspect, which may be carried out using the system shown in FIG. 7, is a method of therapeutic stimulation of a patient's heart which includes the steps of sensing pressure at a site in circulatory system of a patient, comparing mean pressure at the site as determined over a period of predetermined duration with mean pressure at the site as determined over a current period of given duration less than the duration of the period of predetermined duration to find if the determined mean pressures at the site differ by at least a predetermined amount, sensing at least one physiological variable (such as activity level) of the patient; and controlling escape interval or rate of a pacing system alternatively based on the physiological variable whenever the determined mean pressures at the site differ by less than the given amount and based on pressure at the site whenever the mean pressures differ by greater than the given amount.

Figure 8:
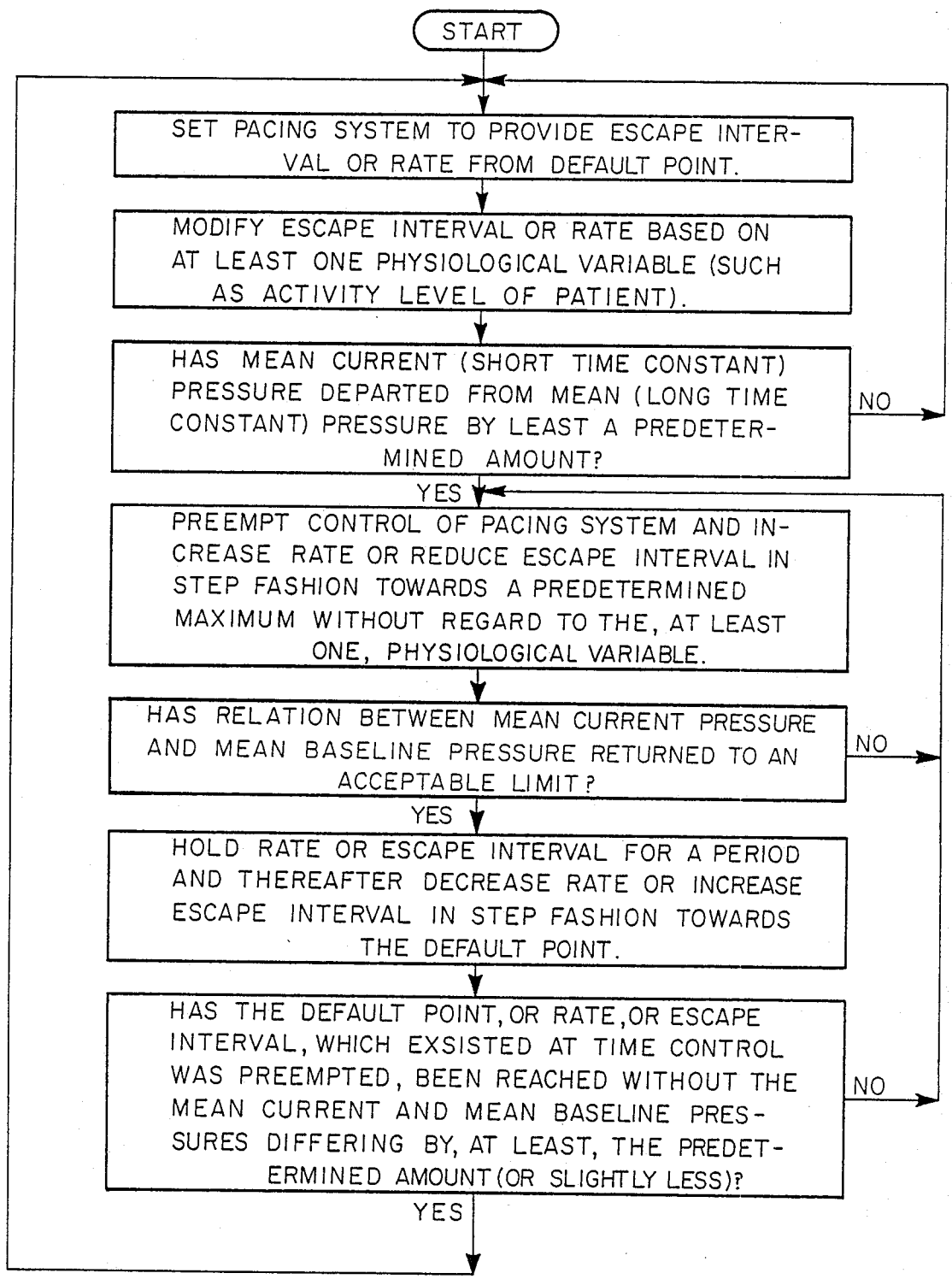
FIG. 8 constitutes a third exemplary flowchart of a series of actions or steps which may be carried out by the systems of the present invention illustrated in FIG. 7 and effect achievement of the third embodiment of the invention in its method aspect.

More particularly, the third embodiment can be seen as a series of steps which are set out in FIG. 8 in the form of a flow chart.

In each method embodiment, it is to be understood that a representation of pressure, as determined over the period of predetermined pressure, can be stored and a representation of the current duration compared therewith, as in the three respective variants of the above-discussed three system embodiments.

Figure 9:
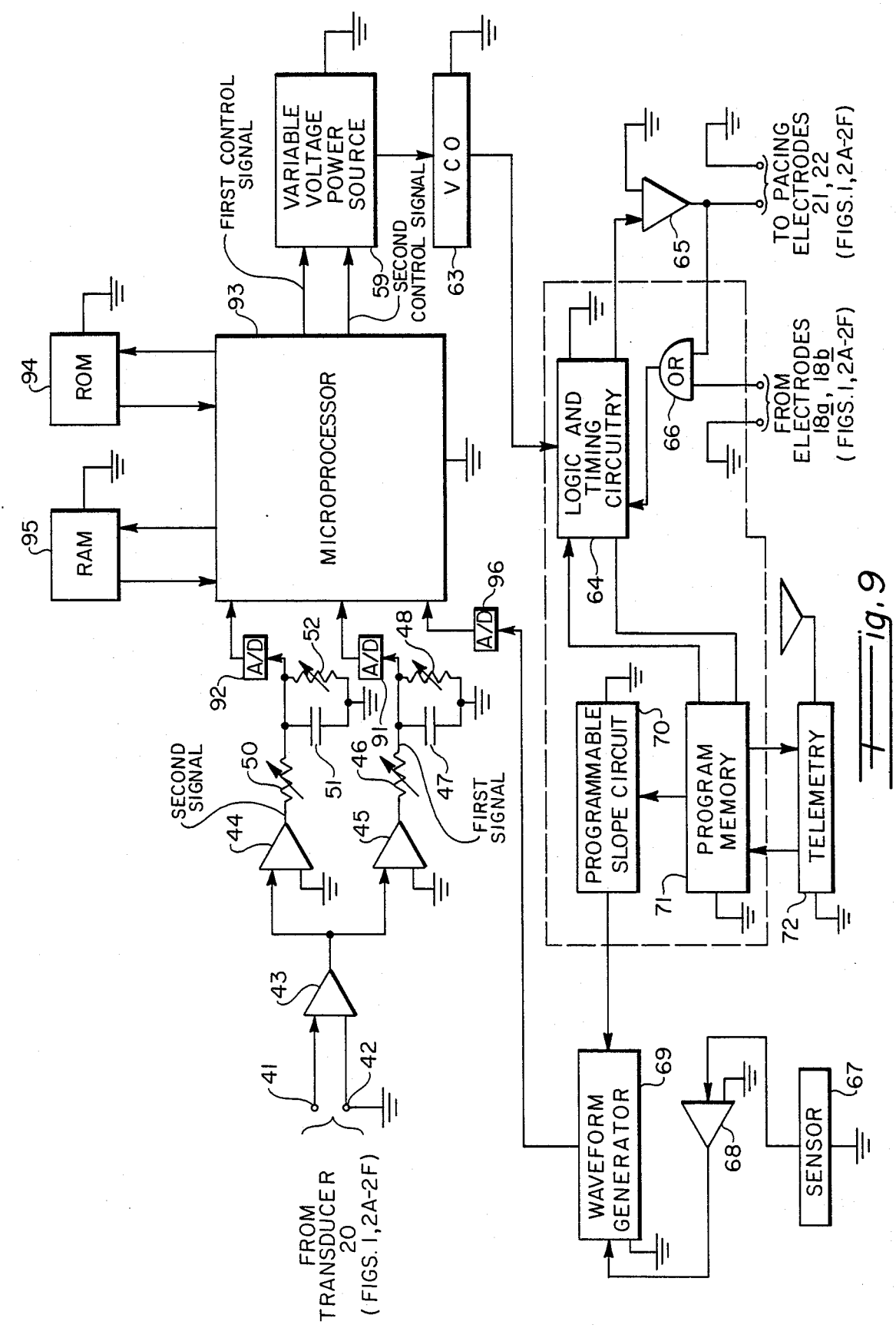
FIG. 9 is a partially block, schematic diagram of a fourth embodiment of an hemodynamic responsive system for therapeutic stimulation of a patient's heart by pacing the malfunctioning heart which provides a microprocessor implementation of the present invention and which can be used to carry out the actions or steps illustrated in FIGS. 4, 6 and 8.

Turning to FIG. 9, a fourth exemplary embodiment of circuit components of a system for treating a malfunctioning heart, which may be positioned within the housing 12 (FIG. 1) includes a pair of input terminals 41, 42 which receive the variable D.C. voltage 30 output signal representing pressure from the pressure responsive transducer 20 (FIGS. 1, 2A-2F), the terminal 42 being connected to a point of circuit reference potential (ground). The terminals 41, 42 are connected to an amplifier 43, which amplifies the pressure representing D.C. input signal and feeds the same to respective buffer amplifiers 44 and 45. The circuit of FIG. 9 can be used in practicing the present invention using either pressure criterion alone or both activity level and pressure criteria (either simultaneously or alternatively). The circuit of FIG. 9 can be used to carry out the methods, illustrated as algorithms in the flowcharts of FIGS. 4, 6 and 8 and can be considered as a digital, microprocessor-based version of the hand-wired analogue circuitry shown in FIGS. 3, 5 and 7. Of course, the microprocessor-based circuit of FIG. 9 could be programmed to carry out other routines. For example, were a rate criterion to be satisfied, the circuit of FIG. 9 could be arranged to effect antitachycardia pacing, were an antitachycardia pacemaker function or separate pacemaker provided. For example, if a tachycardia were detected regardless of whether or not hemodynamic compromise is present an antitachycardia pacemaker would attempt early to revert the heart rate to normal.

The output from the buffer amplifier 45 is supplied to an RC circuit constituted by an adjustable resistor 46 connected to ground via a series connected storage capacitor 47 having a large adjustable resistor 48 connected in parallel therewith. The time constants (charging and discharging) of these circuit components are such that the varying D.C. voltage (first signal) across the capacitor 47 represents the mean pressure sensed by the transducer 20 (FIGS. 1, 2A-2F) over a relatively long period, for example during the preceding fifteen (15) minutes or even longer (for example a number of hours) or shorter (for example 120 seconds) being suitable in some cases. The D.C. voltage (first signal) across the capacitor 47 thus represents a long term mean baseline pressure. The term "mean" as used herein is broad and includes the average value as well as values near the average. The output from the buffer amplifier 44 is supplied to a second RC circuit constituted by an adjustable resistor 50 connected to ground via a capacitor 51, which has an adjustable resistor 52 connected in parallel therewith. The time constants (charging and discharging) of these circuit components are such that the varying D.C. voltage (second signal) which appears across the capacitor 51 represents the short term mean pressure sensed by the transducer 20 (FIGS. 1, 2A-2F) over a relatively short period, for example, during the preceding fifteen (15) seconds or longer (for example 60 seconds) or shorter (for example six seconds).

As illustrated the long term (baseline) and short term (current) D.C. voltage signals (first signal and second signal) which appear across the respective capacitors 47 and 51 are fed respectively via respective analogue-to-digital converters (A/D's) 91 and 92 to respective inputs of a microprocessor 93. The A/D converters 91 and 92, in operation, convert the respective analogue signals which appear across the capacitors 47 and 51 into corresponding digital signals for processing by the microprocessor 93, the microprocessor having associated therewith a ROM 94, which supplies programmed instructions to the microprocessor, and a RAM 95, which stores and supplies digital signal representations of pressure-related signals from and to the microprocessor.

Another input of the microprocessor 93 is supplied with a patient activity level related signal from a third analogue-to-digital converter (A/D) 96 which receives its input from the waveform generator 69. The waveform generator 69 is associated with an activity level sensor 67, an amplifier 68 and a programmable slope circuit 70 which function is the same manner as described above in connection with FIGS. 3 and 5. The slope circuit 70 is associated with a program memory 71 which, in turn, is controlled via telemetry 72 in the same fashion as the circuit components having the same reference numerals as the circuits of FIGS. 3 and 5.

The variable voltage power source 59, the VCO 63, the logic and timing circuitry 64, the amplifier 65 and the OR circuit 66 correspond to and function as do the circuit components having the same reference numerals and shown in FIGS. 5 and 7. In this case the microprocessor 93 produces two outputs (first control signal, second control signal) to the variable voltage power source 59. One effects the setting of the activity level related output which establishes the variable rate baseline shown as the dot-dash line D (FIG. 10) by allowing it to vary as graphically shown by the double-arrow-headed line E (FIG. 10). The other output from the microprocessor 93 effects the step functions graphically represented by the lines A, B and C (FIG. 10).

Figure 4:
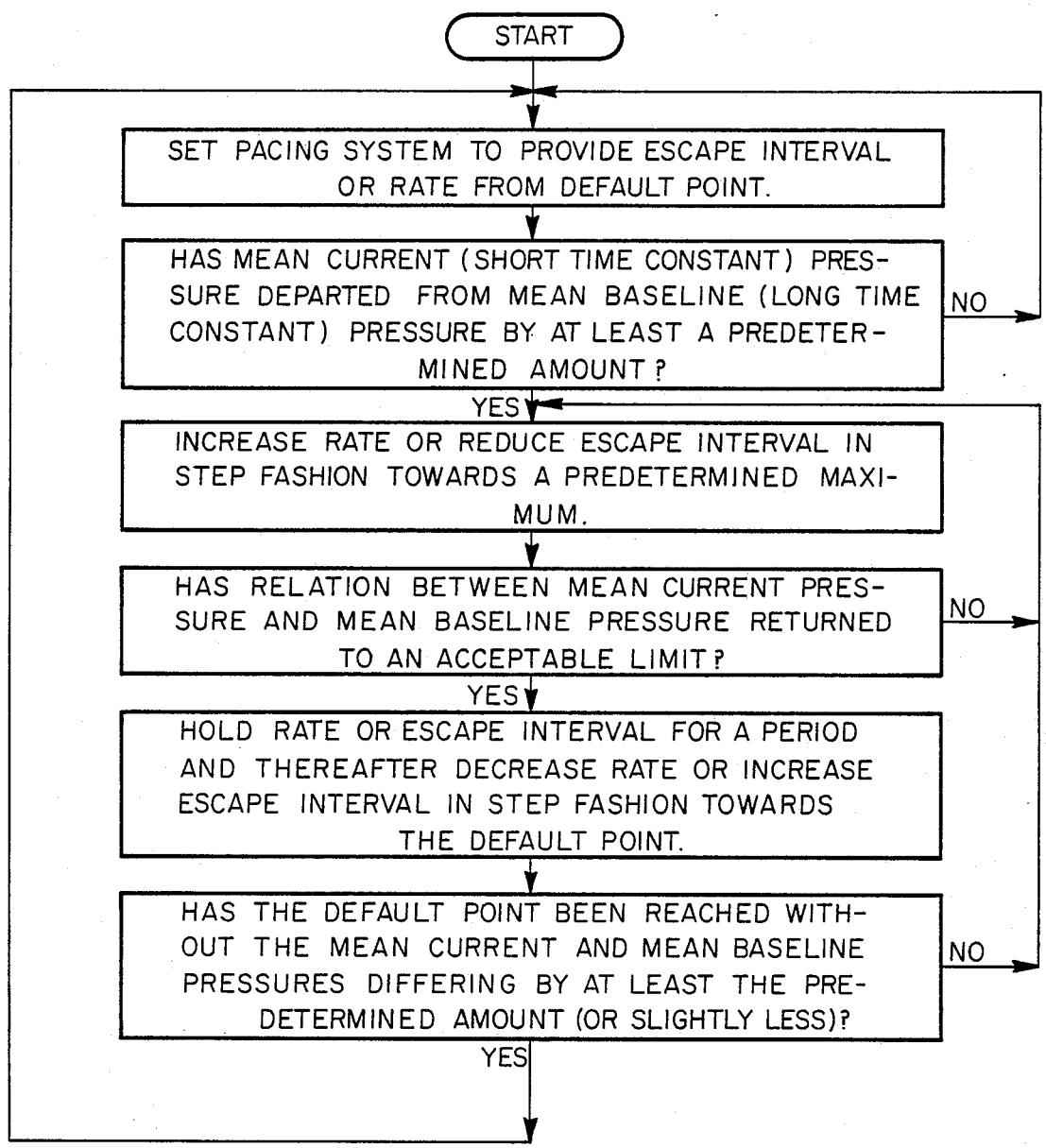
FIG. 4 constitutes a first exemplary flowchart of a series of actions or steps which may be carried out by the system of the present invention illustrated in FIG. 3 and effect achievement of the first embodiment of the invention in its method aspect.

As thus far described, the circuit of FIG. 9 can carry out the methods defined in the flowcharts illustrated in FIGS. 4, 6 and 9, the respective programs being supplied by the ROM 94. In operation, the circuit of FIG. 9 can be seen as a microprocessor realization corresponding to the hand-wired analogue circuits of FIGS. 3, 5 and 7. It is to be appreciated that the circuit of FIG. 9 can be programmed to effect somewhat different routines and be provided with additional inputs, as well.

The foregoing description relates to embodiments of the invention which have been set but by way of example, not by way of description. It is to be understood that numerous other embodiments and variants are possible without departing from the spirit and scope of the invention, its scope being defined by the appended claims.

What is claimed is:

1. In a system for therapeutic stimulation of a patient's heart and which includes means for producing pacing pulses and means for varying the escape interval or rate of said means for producing pacing pulses, an improvement comprising means for sensing blood pressure at a site in the circulatory system of a patient to produce an output, means responsive to the output from the sensing means for developing a variable first signal representative of mean blood pressure at the site over a period of predetermined duration, means responsive to the output from the sensing means for developing a variable second signal representing mean blood pressure at the site over a period of given duration less than the period of predetermined duration, means responsive to the first signal and to the second signal for developing a control signal upon the first signal and the second signal differing by at least a predetermined amount, and means responsive to the control signal for controlling the means for varying the escape interval or rate of the means for producing pacing pulses.

2. The system of claim 1, wherein said means for sensing blood pressure at a site in a circulatory system comprises means for sensing right atrial blood pressure 3. The system of claim 1, wherein said means for sensing blood pressure at a site in a circulatory system comprises means for sensing right ventricular blood pressure 4. The system of claim 1, wherein said means for sensing blood pressure at a site in a circulatory system comprises means for sensing central venous blood pressure 5. The system of claim 1, wherein said means for sensing blood pressure at a site in a circulatory system comprises means for sensing left atrial blood pressure.

6. The system of claim 1, wherein said means for sensing blood pressure at a site in a circulatory system comprises means for sensing left ventricular blood pressure.

7. The system of claim 1, wherein said means for sensing blood pressure at a site in a circulatory system comprises means for sensing arterial blood pressure.

8. The system of claim 1, wherein said means responsive to the first signal and to the second signal for developing a control signal comprise a microprocessor for developing the control signal 9. In a system for therapeutic stimulation of a patient's heart and which includes means for producing pacing pulses and means for varying the escape interval or rate of said means for producing pacing pulses, an improvement comprising means for sensing blood pressure at a site in the circulatory system of a patient to produce an output, means responsive to the output from the sensing means for developing a variable first signal representative of mean blood pressure at the site over a period of predetermined duration, means responsive to the output from the sensing means for developing a variable second signal representative of mean blood pressure at the site over a period of give duration less than the period of predetermined duration, means responsive to the first signal and to the second signal for developing a first control signal whenever the first signal and the second signal differ by at least a predetermined amount, means responsive to a signal dependent on at least one physiological variable for developing a second control signal, and means contemporaneously responsive to the first control signal and to the second control signal for conjointly controlling the means for producing pacing pulses for modifying the escape interval or rate thereof.

10. The system of claim 9, wherein said means for sensing blood pressure at a site in a circulatory system comprises means for sensing right atrial blood pressure.

11. The system of claim 9, wherein said means for sensing blood pressure at a site in a circulatory system comprises means for sensing right ventricular blood pressure.

12. The system of claim 9, wherein said means for sensing blood pressure at a site in a circulatory system comprises means for sensing central venous blood pressure.

13. The system of claim 9, wherein said means for sensing blood pressure at a site in a circulatory system comprises means for sensing left atrial blood pressure.

14. The system of claim 9, wherein said means for sensing blood pressure at a site in a circulatory system comprises means for sensing left ventricular blood pressure.

15. The system of claim 9, wherein said means for sensing blood pressure at a site in a circulatory system comprises means for sensing arterial blood pressure.

16. The system of claim 9, wherein said means responsive to the first signal and to the second signal for developing a control signal comprises a microprocessor for developing the control signal.

17. The system of claim 9, including means for sensing activity level of a patient as the physiological variable to produce an output, and means responsive to the output from the means for sensing activity level to develop the second control signal.

18. A method of therapeutic stimulation of a patient's heart comprising:
    sensing blood pressure at a site in circulation system of a patient;
    comparing means sensed blood pressure at the site as determined over a period of predetermined duration with mean sensed blood pressure at the site as determined over a current period of given duration less than the duration of the period of predetermined duration to find if the determined mean blood pressures at the site differ by at least a predetermined amount; and
    controlling the escape interval or rate of a pacing system whenever the mean pressures differ by at least the predetermined amount.

19. The method of claim 18, wherein the step of sensing blood pressure is constituted by sensing right atrial blood pressure.

20. The method of claim 18, wherein the step of sensing blood pressure is constituted by sensing right ventricular blood pressure.

21. The method of claim 18, wherein the step of sensing blood pressure is constituted by sensing central venous blood pressure.

22. The method of claim 18, wherein the step of sensing blood pressure is constituted by sensing left atrial blood pressure.

23. The method of claim 18, wherein the step of sensing blood pressure is constituted by sensing left ventricular blood pressure.

24. The method of claim 18, wherein the step of sensing blood pressure is constituted by sensing arterial pressure.

25. A method of therapeutic stimulation of a patient's heart comprising:
    sensing blood pressure at a site in circulatory system of a patient;
    comparing means blood pressure at the site as determined over a period of predetermined duration with means blood pressure at the site as determined over a current period of given duration less than the duration of the period of predetermined duration to find if the determined means blood pressures at the site differ by at least a predetermined amount;
    sensing at least one physiological variable of the patient; and
    controlling the escape interval or rate of a pacing system contemporaneously based on the physiological variable and on the determined mean blood pressures at the site.

26. The method according to claim 25, wherein the step of sensing at least one physiological variable is constituted by sensing vibrational energy at a site in or on the patient and converting the sensed energy into an activity related signal.

27. The method of claim 25 wherein the step of sensing blood pressure is constituted by sensing right atrial blood pressure.

28. The method of claim 25, wherein the step of sensing blood pressure is constituted by sensing right ventricular blood pressure 29. The method of claim 25, wherein the step of sensing blood pressure is constituted by sensing central venous blood pressure.

30. The method of claim 25, wherein the step of sensing blood pressure is constituted by sensing left atrial blood pressure.

31. The method of claim 25, wherein the step of sensing blood pressure is constituted by sensing left ventricular blood pressure.

32. The method of claim 25, wherein the step of sensing blood pressure is constituted by sensing arterial blood pressure.

33. In a system for therapeutic stimulation of a patient's heart and which includes means for producing pacing pulses and means for varying the escape interval or rate of said means for producing pacing pulses, an improvement comprising means for sensing blood pressure at a site in the circulatory system of a patient to produce an output, means responsive to the output from the sensing means for developing a variable first signal representative of mean blood pressure at the site over a period of predetermined duration, means responsive to output from the sensing means for developing a variable second signal representing means blood pressure at the site over a period of given duration less than the period of predetermined duration, means responsive to the variable first signal and to the variable second signal for developing a stored first signal upon the first signal and the second signal differing by at least a predetermined amount, means responsive to the stored first signal and to the second signal for developing a control signal upon the stored first signal and the second signal differing by at least a given amount, and means responsive to the control signal for controlling the means for varying the escape interval or rate of the means for producing pacing pulses.

34. The system according to claim 33, wherein the predetermined amount is greater than the given amount.

35. In a system for therapeutic stimulation of a patient's heart and which includes mean for producing pacing pulses and means for varying the escape interval or rate of a means for producing pacing pulses, an improvement comprising means for sensing blood pressure at a site in the circulatory system of a patient to produce an output, means responsive to the output from the sensing means for developing a variable first signal representative of mean blood pressure at the site over a period of predetermined duration, means responsive to the output from the sensing means for developing a variable second signal representative of mean blood pressure at the site over a period of given duration less than the period of predetermined duration, means responsive to the variable first signal and to the variable second signal for developing a stored first signal upon the first signal and the second signal differing by at least a predetermined amount, means responsive to the first signal and to the second signal for developing a first control signal whenever the stored first signal and the second signal differ by at least a given amount, means responsive to a signal dependent on at least one physiological variable for developing a second control signal, and means contemporaneously responsive to the first control signal and to the second control signal for conjointly controlling the means for producing pacing pulses for modifying the escape interval or rate thereof, whereby the escape interval or rate may be determined contemporaneously by the at least one physiological variable and by hemodynamic pressure at a site in the circulatory system.

36. The system according to claim 35, wherein the predetermined amount is greater than the given amount.

37. A method of therapeutic stimulation of a patient's heart comprising:
sensing blood pressure at a site in circulation system of a patient;
comparing mean sensed blood pressure at the site as determined over a period of predetermined duration with mean sensed blood pressure at the site as determined over a current period of given duration less than the duration of the period of predetermined duration to find if the determined mean pressures at the site differ by at least a predetermined amount;
storing a representation of the mean sensed blood pressure at the site as determined over a period of predetermined duration at the time the sensed mean blood pressures differed by at least the predetermined amount;
comparing the stored representation of the sensed mean blood pressure with mean sensed blood pressure at the site as determined over a current period of the given duration to determine if current means blood pressure at the site differs from the stored representation by at least a give amount; and
controlling the escape interval or rate of a pacing system whenever current mean blood pressure differs from the stored representation of mean blood pressure by at least the given amount.

38. A method of therapeutic stimulation of a patient's heart comprising:
sensing blood pressure at a site in circulatory system of a patient;
comparing means blood pressure at the site as determined over a period of predetermined duration with mean blood pressure at the site as determined over a current period of given duration less than the duration of the period of predetermined duration to find it the determined mean blood pressures at the site differ by at least a predetermined amount;
storing a representation of the mean sensed blood pressure at the site as determined over a period of predetermined duration at the time the sensed mean blood pressures differed by at least the predetermined amount;
comparing the stored representation of the sensed mean blood pressure with mean sensed blood pressure at the site as determined over a current period of the given duration to determine if current mean blood pressure at the site differs from the stored representation by at least a given amount;
sensing at least one physiological variable of the patient; and
controlling the escape interval or rate of a pacing system contemporaneously based on the physiological variable and determine the current mean pressure differing from the stored representation of mean pressure by at least the given amount.

39. In a system for therapeutic stimulation of a patient's heart and which includes means for varying escape interval or rate of a means for producing pacing pulses, an improvement comprising means for sensing hemodynamic pressure at a site in the circulatory system of a patient, means responsive to output from the sensing means for developing a variable first signal representative of mean pressure at the site over a period of predetermined duration, means responsive to output from the sensing means for developing a variable second signal representative of mean pressure at the site over a period of given duration less than the period of predetermined duration, means responsive to the variable first signal and to the variable second signal for developing a stored first variable signal upon the first variable signal and the second variable signal differing by at least a predetermined amount, means responsive to the first variable signal and to the second variable signal for developing a stored first variable signal upon the first variable signal and the second variable signal differing by at least a predetermined amount, means responsive to the first variable signal and to the second variable signal for developing a first control signal whenever the stored first variable signal and the second variable signal differ by at least a given amount, and means responsive to a signal dependent on at least one physiological variable for developing a second control signal, said means for varying escape interval or rate being contemporaneously responsive to the first control signal and to the second control signal for conjointly controlling the means for producing pacing pulses for modifying the escape interval or rate thereof; whereby the escape interval or rate may be determined contemporaneously by said at least one physiological variable and said hemodynamic pressure at a site in the circulatory system.

40. The system according to claim 39, wherein the predetermined amount is greater than the given amount.

* * * * *